(12) United States Patent
Bettinger et al.

(10) Patent No.: US 8,691,203 B2
(45) Date of Patent: *Apr. 8, 2014

(54) METHOD COMPRISING CONTACTING TISSUE WITH A CROSS-LINKABLE POLYESTER PREPOLYMER

(75) Inventors: Christopher J. Bettinger, Palo Alto, CA (US); Joost P. Bruggeman, Schorl (NL); Lino Da Silva Ferreira, Coimbra (PT); Jeffrey M. Karp, Chestnut Hill, MA (US); Robert S. Langer, Newton, MA (US); Christiaan Nijst, Amsterdam (NL); Andreas Zumbuehl, Nyon (CH); Jason Burdick, Philadelphia, PA (US); Sonia J. Kim, West Nyack, NY (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,869

(22) Filed: Mar. 23, 2012

(65) Prior Publication Data
US 2012/0269761 A1 Oct. 25, 2012

Related U.S. Application Data

(63) Continuation of application No. 11/623,041, filed on Jan. 12, 2007, now Pat. No. 8,143,042.

(60) Provisional application No. 60/758,973, filed on Jan. 12, 2006, provisional application No. 60/803,223, filed on May 25, 2006.

(51) Int. Cl.
| | | |
|---|---|---|
| *A61K 31/74* | (2006.01) | |
| *A61F 2/00* | (2006.01) | |
| *A61K 9/52* | (2006.01) | |
| *A61K 9/14* | (2006.01) | |
| *C12N 11/08* | (2006.01) | |
| *C12N 11/04* | (2006.01) | |
| *C12N 5/00* | (2006.01) | |
| *C12N 5/07* | (2010.01) | |

(52) U.S. Cl.
USPC ........ 424/78.06; 424/423; 424/457; 424/486; 424/487; 424/93.1; 424/93.7; 435/180; 435/182; 435/395; 528/272

(58) Field of Classification Search
None
See application file for complete search history.

(56) References Cited

U.S. PATENT DOCUMENTS

| | | |
|---|---|---|
| 1,489,744 A | 4/1924 | Downs |
| 1,779,367 A | 10/1930 | Bruson |
| 3,772,064 A | 11/1973 | Mendelsohn |
| 4,048,256 A | 9/1977 | Casey |
| 4,064,086 A | 12/1977 | Cowsar |
| 4,177,596 A | 12/1979 | Dillow |
| 4,205,399 A | 6/1980 | Shalaby |
| 4,275,169 A | 6/1981 | Rudner |
| 4,343,048 A | 8/1982 | Ross |
| 4,638,045 A | 1/1987 | Kohn |
| 4,806,621 A | 2/1989 | Kohn |
| 4,946,929 A | 8/1990 | DAmore |
| 5,010,167 A | 4/1991 | Ron |
| 5,019,379 A | 5/1991 | Domb |
| 5,116,937 A | 5/1992 | Greene |
| 5,166,310 A | 11/1992 | Rooney |
| 5,286,763 A | 2/1994 | Gerhart |
| 5,295,985 A | 3/1994 | Romesser |
| 5,399,665 A | 3/1995 | Barrera |
| 5,489,298 A | 2/1996 | Love |
| 5,505,808 A | 4/1996 | Hallman |
| 5,512,600 A | 4/1996 | Mikos |
| 5,514,378 A | 5/1996 | Mikos |
| 5,525,646 A | 6/1996 | Lundgren |
| 5,545,212 A | 8/1996 | Wakabayashi |
| 5,696,175 A | 12/1997 | Mikos |
| 5,716,404 A | 2/1998 | Vacanti |
| 5,736,372 A | 4/1998 | Vacanti |
| 5,770,417 A | 6/1998 | Vacanti |
| 5,804,178 A | 9/1998 | Vacanti |
| 5,837,752 A | 11/1998 | Shastri |

(Continued)

FOREIGN PATENT DOCUMENTS

| | | |
|---|---|---|
| EP | 0246341 | 11/1987 |
| EP | 0427496 | 5/1991 |

(Continued)

OTHER PUBLICATIONS

Amsden, et al., "In vivo degradable behavior of photo-cross-linked star-poly(e-caprolactone-co-D,L-lactide) elastomers", Biomacromolecules, 7:365-372 (2006).
Amsden, et al., "Synthesis and characterization of a photo-cross-linked biodegradable elastomer", Biomacromolecules, 5:2479-2486 (2004).
Anderson, "In vivo biocompatibility of implantable delivery systems and biomaterials", Eur. J. Pharm. Biopharm., 40:1-8 (1994).
Anderson, et al., "Biodegradation and biocompatibility of PLA and PLGA microspheres", Advanced Drug Delivery Reviews,#s(3A#5-24 (1997).
Anseth, et al. 'Photopolymerizable degradation polyanhydrides with osteocompatibility', Nature Biotechnology, 17:156-159(1999).
Barera, et al., 'Synthesis and RGD peptide medication of a new biodegradable copolymer: Poly(lactic acid c-lysine)', JACS, 115:11010-11011 (1993).
Cadee, et al., "A comparative biocompatibility study of microspheres based on crosslinked dextran or poly(lactic-co-glycolic) acid after subcutaneous injection in rats", J Biomed. Muter. Res. 56:600-609 (2001).

(Continued)

*Primary Examiner* — David M Naff
(74) *Attorney, Agent, or Firm* — Pabst Patent Group LLP

(57) ABSTRACT

The present inventions in various aspects provide elastic biodegradable polymers. In various embodiments, the polymers are formed by the reaction of a multifunctional alcohol or ether and a difunctional or higher order acid to form a prepolymer, which is cross-linked to form the elastic biodegradable polymer. In preferred embodiments, the cross-linking is performed by functionalization of one or more OR groups on the pre-polymer backbone with vinyl, followed by photopolymerization to form the elastic biodegradable polymer composition or material. Preferably, acrylate is used to add one or more vinyls to the backbone of the pre-polymer to form an acrylated pre-polymer. In various embodiments, acrylated pre-polymers are co-polymerized with one or more acrylated co-polymers.

17 Claims, 20 Drawing Sheets

(56) References Cited

U.S. PATENT DOCUMENTS

| | | | |
|---|---|---|---|
| 5,902,599 | A | 5/1999 | Anseth |
| 6,017,566 | A | 1/2000 | Buncek |
| 6,095,148 | A | 8/2000 | Shastri |
| 6,123,727 | A | 9/2000 | Vacanti |
| 6,160,084 | A | 12/2000 | Langer |
| 6,376,742 | B1 | 4/2002 | Zdrahala |
| 6,444,782 | B1 | 9/2002 | Hamlin |
| 6,818,018 | B1 | 11/2004 | Sawhney |
| 6,984,393 | B2 | 1/2006 | Amsden |
| 7,192,604 | B2 | 3/2007 | Brown |
| 8,143,042 | B2 * | 3/2012 | Bettinger et al. ............. 435/180 |
| 2002/0049183 | A1 | 4/2002 | Yedgar |
| 2003/0003125 | A1 | 1/2003 | Nathan |
| 2003/0086985 | A1 | 5/2003 | Gupta |
| 2003/0118692 | A1 | 6/2003 | Wang |
| 2003/0185870 | A1 | 10/2003 | Grinstaff |
| 2004/0006153 | A1 | 1/2004 | Seppala |
| 2004/0086479 | A1 | 5/2004 | Grinstaff |
| 2004/0131582 | A1 | 7/2004 | Grinstaff |
| 2005/0019747 | A1 | 1/2005 | Anderson |
| 2005/0048121 | A1 | 3/2005 | Kanamathareddy |
| 2005/0063939 | A1 | 3/2005 | Ameer |
| 2008/0081074 | A1 | 4/2008 | Gu |
| 2008/0274979 | A1 | 11/2008 | Ellis-Behnke |
| 2009/0011486 | A1 | 1/2009 | Bettinger |
| 2009/0047256 | A1 | 2/2009 | Bettinger |

FOREIGN PATENT DOCUMENTS

| | | |
|---|---|---|
| EP | 0509814 | 10/1992 |
| EP | 0711506 | 5/1996 |
| EP | 0786329 | 7/1997 |
| EP | 0807653 | 11/1997 |
| EP | 0934918 | 8/1999 |
| EP | 1038538 | 9/2000 |
| JP | 57170259 | 10/1982 |
| JP | 5140870 | 6/1993 |
| WO | 9830617 | 7/1998 |
| WO | 9858010 | 12/1998 |
| WO | 0035297 | 6/2000 |
| WO | 0176554 | 10/2001 |
| WO | 03064496 | 8/2003 |

OTHER PUBLICATIONS

Calandrelli, et al., "Preparation and characterization of composites based on biodegradable polymers for 'in vivo' application", Polymer, 41: 80-8033 (2000).

Dupont-Gillain, et al., "Collagen adsorption on poly(methyl methacrylate): net like structure formation upon drying", Polymer Int. 48:271-276 (1999).

Frazl, et al., "Fibrillar structure and mechanical properties of collagen", J. of Struc. Biol., 122:119-122 (1997).

Gao, et al. "Surface hydrolysis of poly(glycolic acid) meshes increases the seeding density of vascular smooth muscle cells", Journal of Biomedical Materials Research 42: 417-424 (1998).

Groot, et al., 'Use of porous polyurethanes for meniscal reconstruction and meniscal prostheses', Biomaterials, 17:163-173(1996).

Gu, et al., "Sustained interferon-y delivery from a photocrosslinked biodegradable elastomer", J. Contr. Release, 102:607-617(2005).

Guan, et al., 'Biodegradable poly(ether ester urethane)urea elastomers based on poly (ether ester) triblock copolymers and putrescine: synthesis, characterization and cytocompatibility', Biomaterials, 25(1):85-96 (2004).

Guan, et al., "Synthesis, characterization, and cytocompatibility of elastomeric, biodegradable poly(ester-urethane)ureas based on poly(caprolactone) and putrescine", J. Biomed. Mater. Res., 61(3):493-503 (2002).

Helminen, et al., "Biodegradable crosslinked polymers based on triethoxysilane terminated polyactice oligomers", Polymer, 42:3345-3353 (2001).

Jayachandran, et al., "Synthesis of dense brush polymers with cleavable grafts", European Polymer Journal 36:743-749 (2000).

Kiyotsukuri, et al., 'Network polyester films from glycerol and dicarboxylic acids', Polymer International, 33(1): 1-8 (1994).

Langer, "Biomaterials: status, challenges, and perspectives", AIChE Journal, 46:1286-1289 (2000).

Laschewsky et al., 'Tailoring of stimuli-responsive water soluble acrylamide and methacrylamide polymers', Macromol. Chem. Phys., 202:276-286 (2001).

Lee, et al., "Controlling mechanical and swelling properties of algmate hydrogels independently by cross-linker type and cross-linking density", Macromolecules, 33:4291 4294 (2000).

Liu, et al., 'Mechanisms for the transport of a, W-Dicarboxylates through the mitochondrial inner membrane', The Journal of Biological Chemistry 211:25338-25344 (1996).

Malekzadeh, et al., 'Isolation of human osteoblast-like cells and in vitro amplification for tissue engineering', Journal of Periodontology 69: 1256-1262 (1998) (abstract only).

Middleton, et al., "Synthetic biodegradable polymers as orthopedic devices", Biomaterials, 21:2335-2346 (2000).

Misof, et al., "A new molecular model for collagen elasticity based on synchrotron x-ray scattering evidence", Biophysical Journal, 72:1376-1381 (1997).

Mitsunobu & Yamada, "Preparation of esters of carboxylic and phosphoric acid via quaternary phosphonium salts," Bullet. Chem. Soc. Japan, 40 (10):2380-2382 (1967).

Motlagh, et al., 'Hemocompatibility evaluation of poly(glycerol-sebacate) in vitro for vascular tissue engineering', Biomaterials, 27(24):4315-24 (2006). Epub May 3, 2006.

Nagata, et al., "Synthesis, characterization, and enzymatic degradation of network aliphatic copolyesters", Journal of Polymer Science: Part A: Polymer Chemistry 37: 2005-2011 (1999).

Pego, et al., 'In vitro degradation of triethylene carbonate based (co)polymers', Macromol. Biosci., 2(9):411-419 (2002).

Pego, et al., 'In vivo behavior of poly(I,3-trimethylene carbonate and copolymers of 1,3-trimethylene carbonate with D,L-lactide or c-caprolactone: Degradation and tissue response', J. Biomed. Mater. Res. A., 67(3):1044-54 (2003).

Pego, et al., "Biodegradable elastomeric scaffolds for soft tissue engineering", J. Contr. Release, 87:69-79 (2003).

Peppas, et al., "New challenges in biomaterials", Science, 263:1715-1720 (1994).

Rosenblatt, et al., 'Synthesis of a fragment of human parathyroid hormore, hPTH-(44-68)', J. Med. Chem., 20(11):1452-6 (1977).

Semba, et al., "Acute rupture of the descending thoracic oarta: repair with use of endovascular stent-grafts", Journal of Vascular and Intewentional Radiology, 8:337-342, (1997) (abstract only).

Storey, et al., "Methacrylate-endcapped poly(d,l-lactide-co-trimethylene carbonate) oligmers. Network formation by thermal free-radical curing", Polymer, 38:6295-6301 (1997).

Sundback, et al., "Biocompatibility analysis of poly(glycerol sebacate) as a nerve guide material", Biomaterials, 26:5454-64 (2005).

Tamada, et al., "The development of polyanhydrides for drug delivery applications", J. Biomater Sci. Polymer Edn., 3:315-353 (1992).

Van Der Elst et al., "Bone tissue response to biodegradable polymers used for intramedullary fracture fixation: A long-term in vivo study in sheep femora", Biomaterials, 20:121-128 (1999).

Wang, et al., 'In vivo degradation characteristics of poly(glycerol sebacate)', J. Biomed. Mater. Res. A., 66(1): 192-7 (2003).

Wang, et al., "A tough biodegradable elastomer", Nat. Biotechnol., 20(6):602-6 (2002).

Wang, et al., "Failure criterion of collagen fiber: Viscoelastic behavior simulated by using load control data", Theoretical and Applied Facture Mechanics, 27:1-12 (1997).

West, et al., "Polymeric biomaterials with degradation sites for proteases involved in cell migration", Macromolecules, 32:241-244 (1999).

Yang, et al., "Novel citric acid-based biodegradable elastomers for tissue engineering", Adv. Mater. 16(6):511-16 (2004).

Yang, et al., "Synthesis and evaluation of poly(diol citrate) biodegradable elastomers", Biomaterials, 27(9): 1889-98 (2006).

* cited by examiner

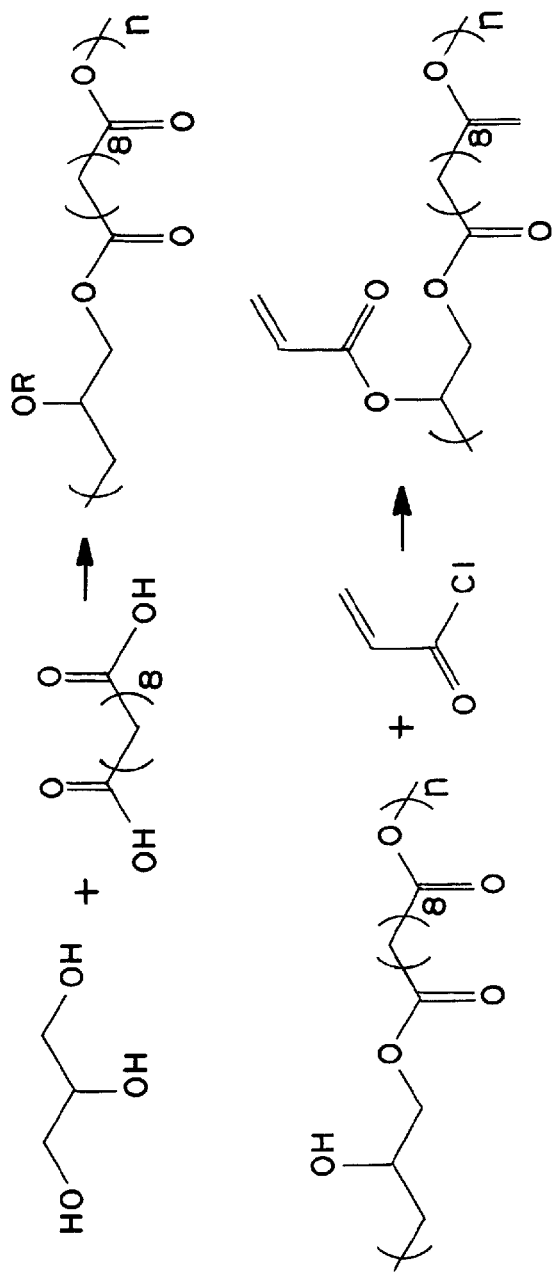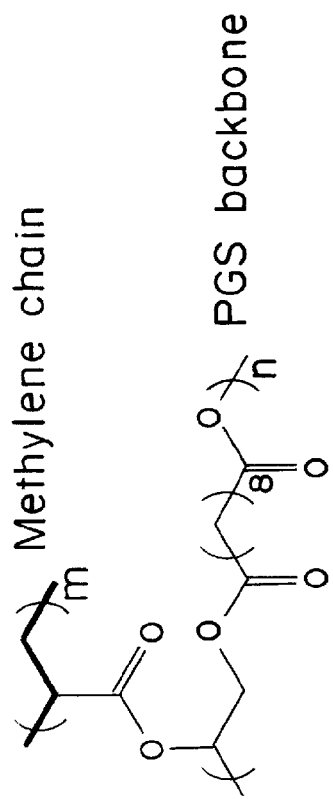
FIG. 3A
FIG. 3B
FIG. 3C

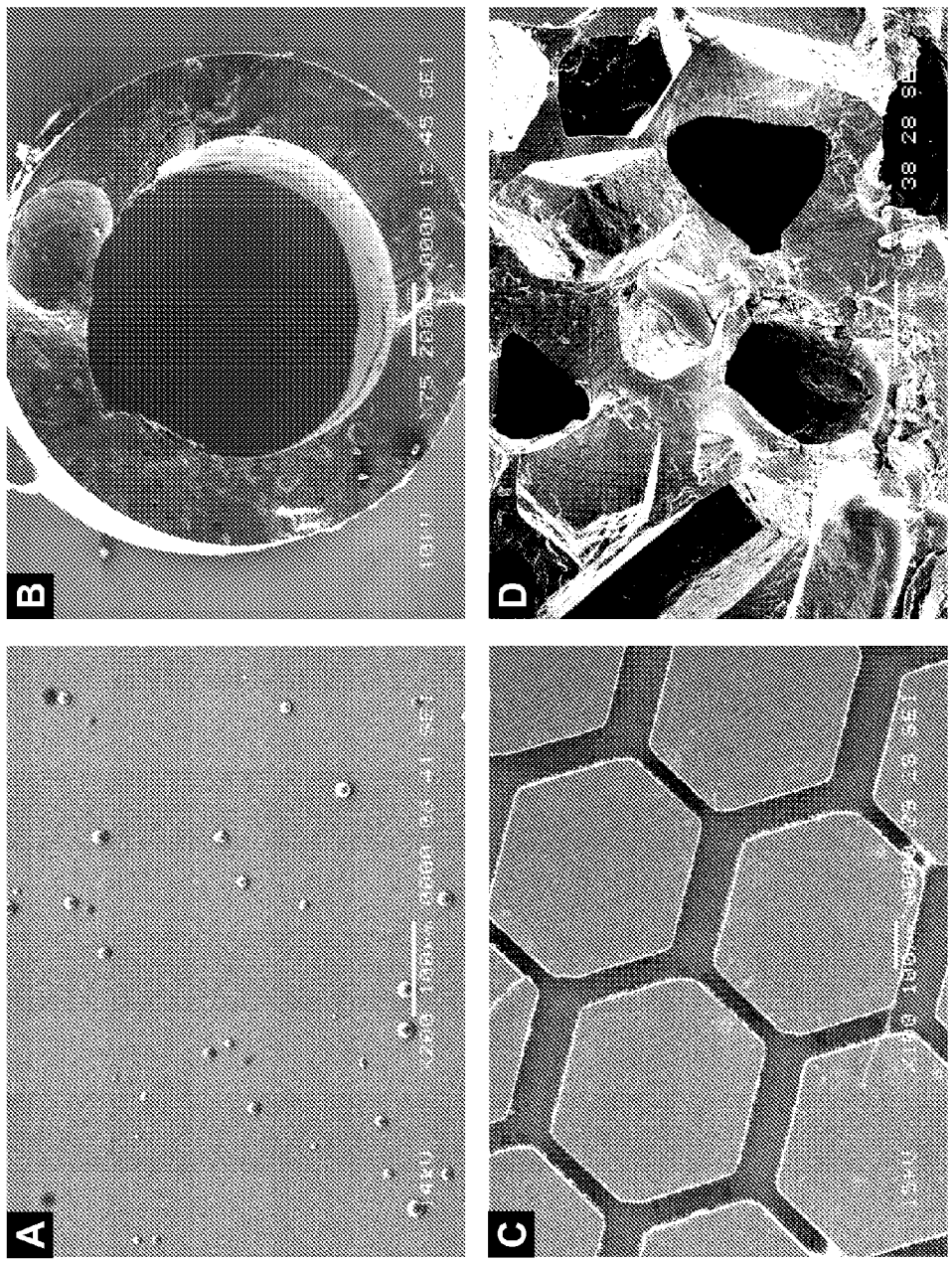
FIGURES 7A-D

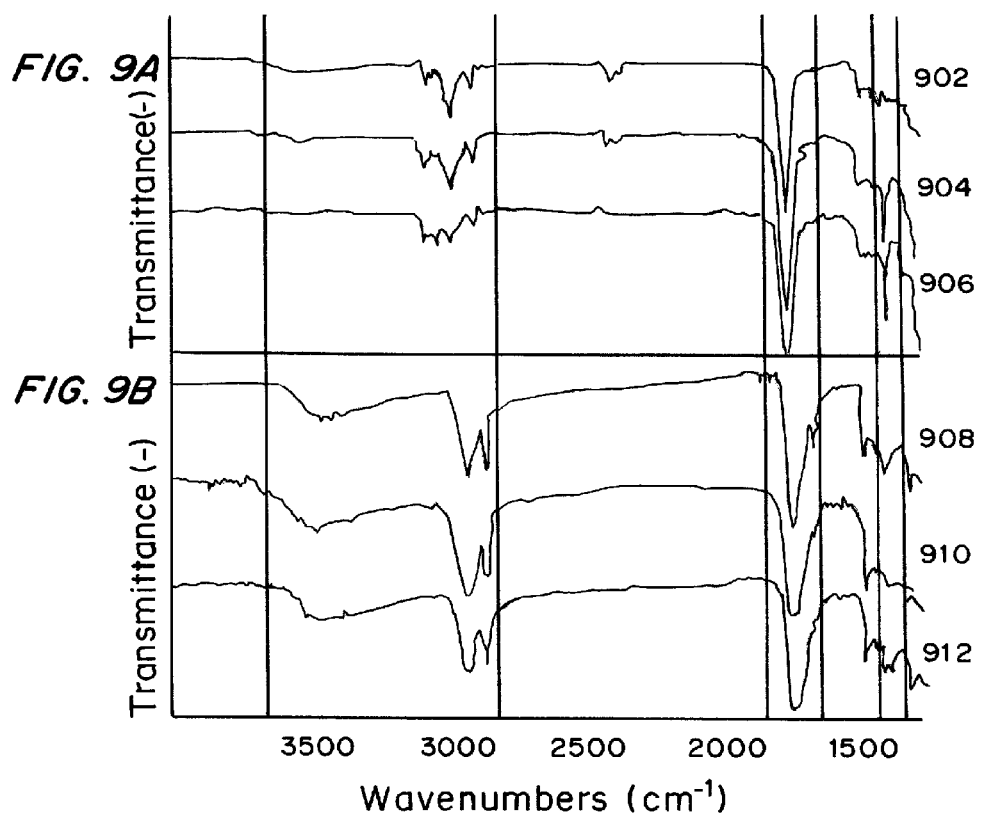

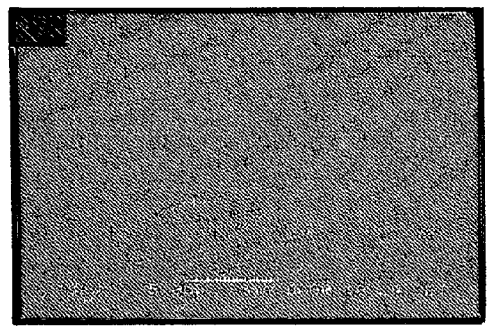 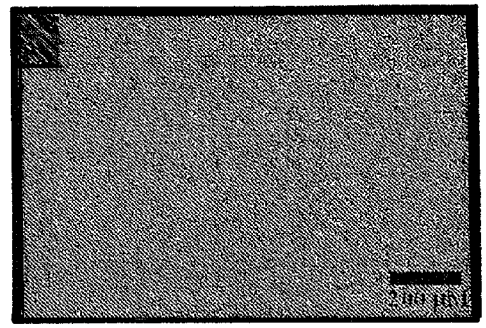
FIG. 14A  FIG. 14B
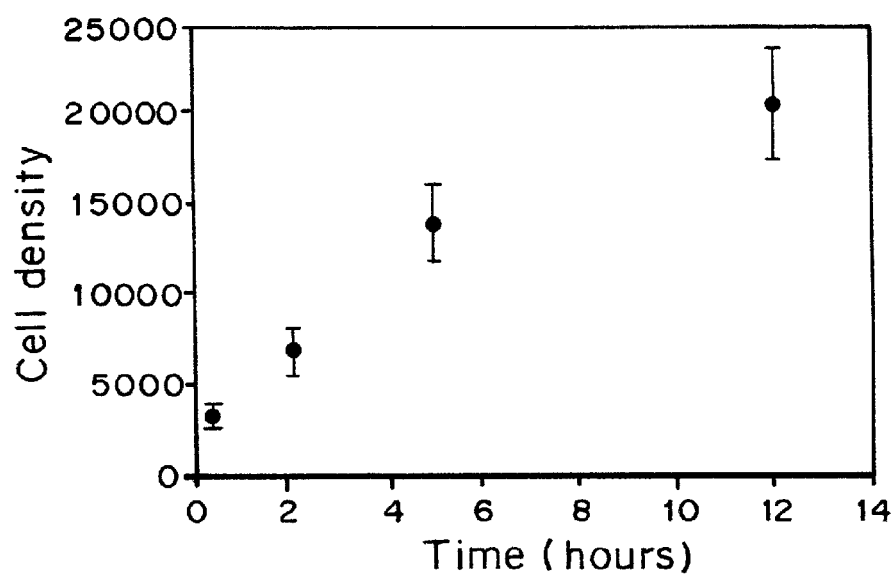
FIG. 14C

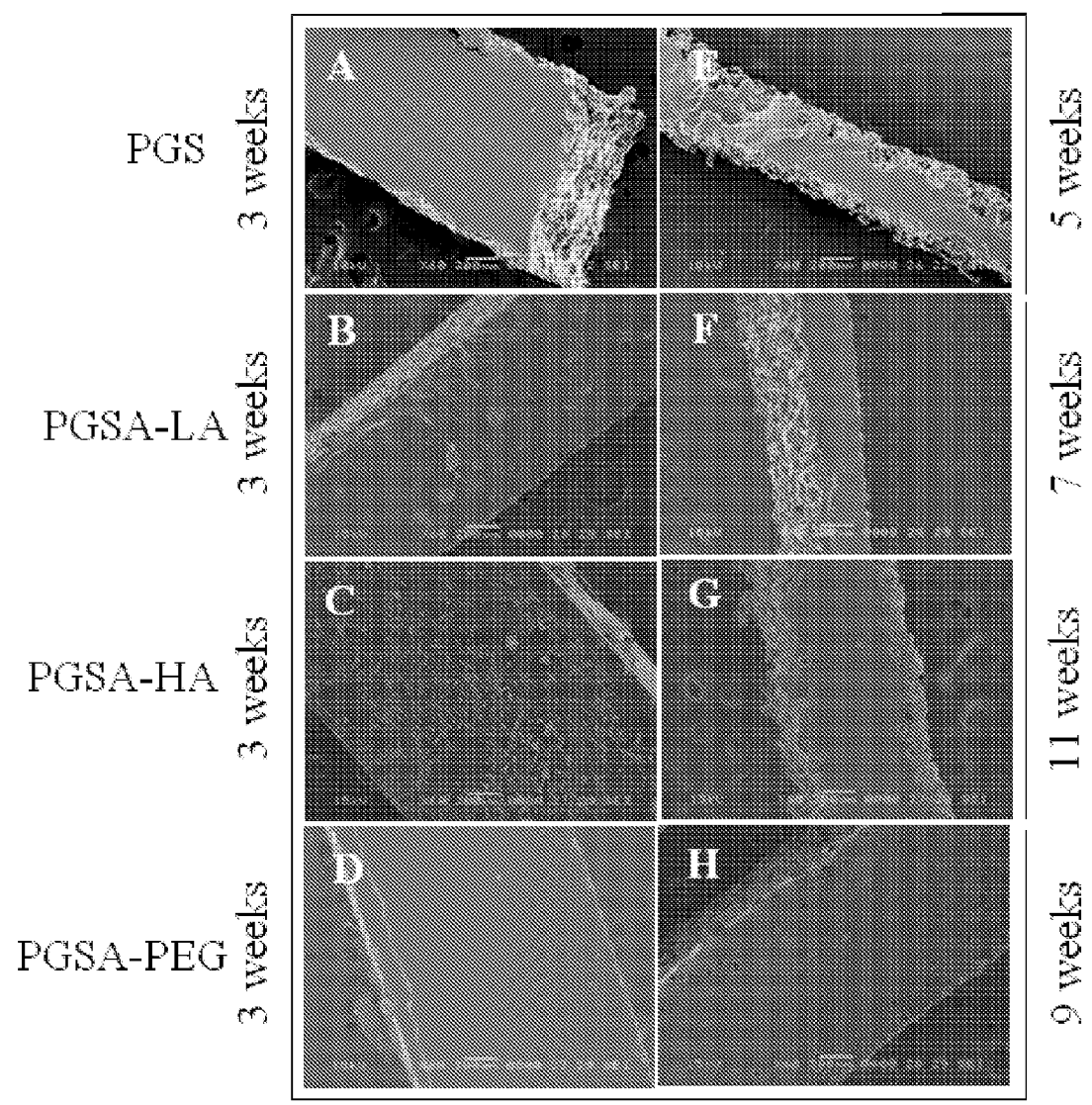
FIGURES 18A-H

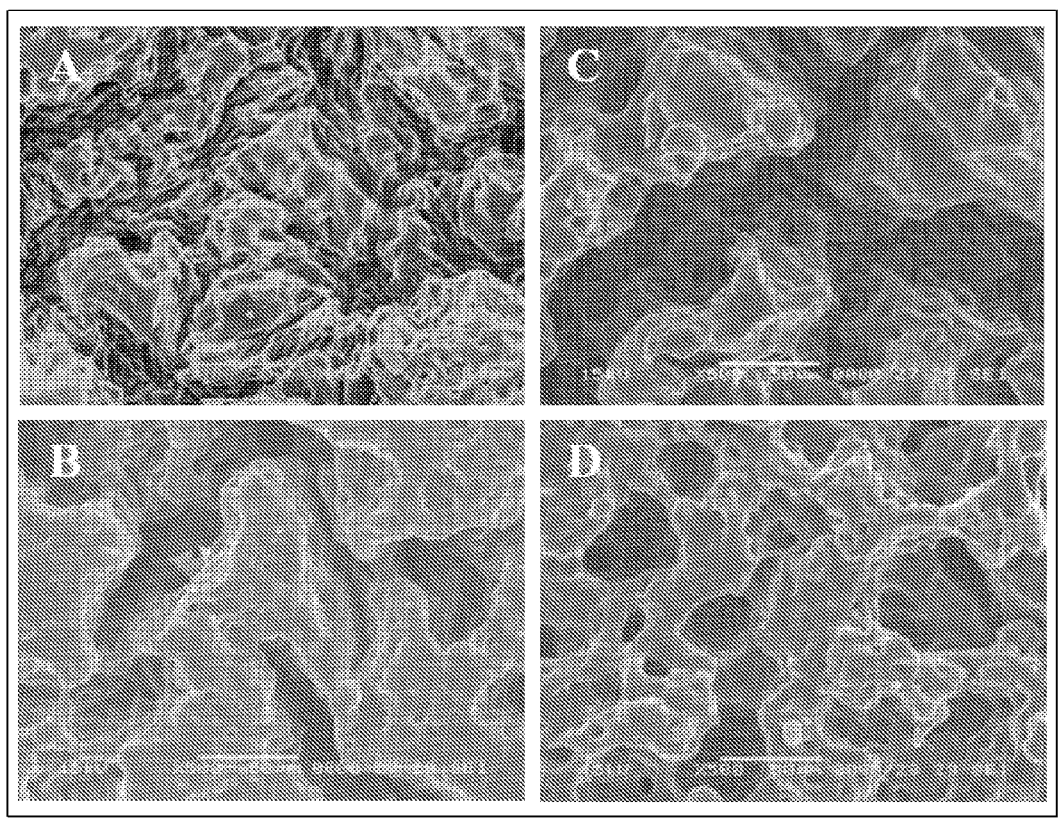
FIGURES 19A-D

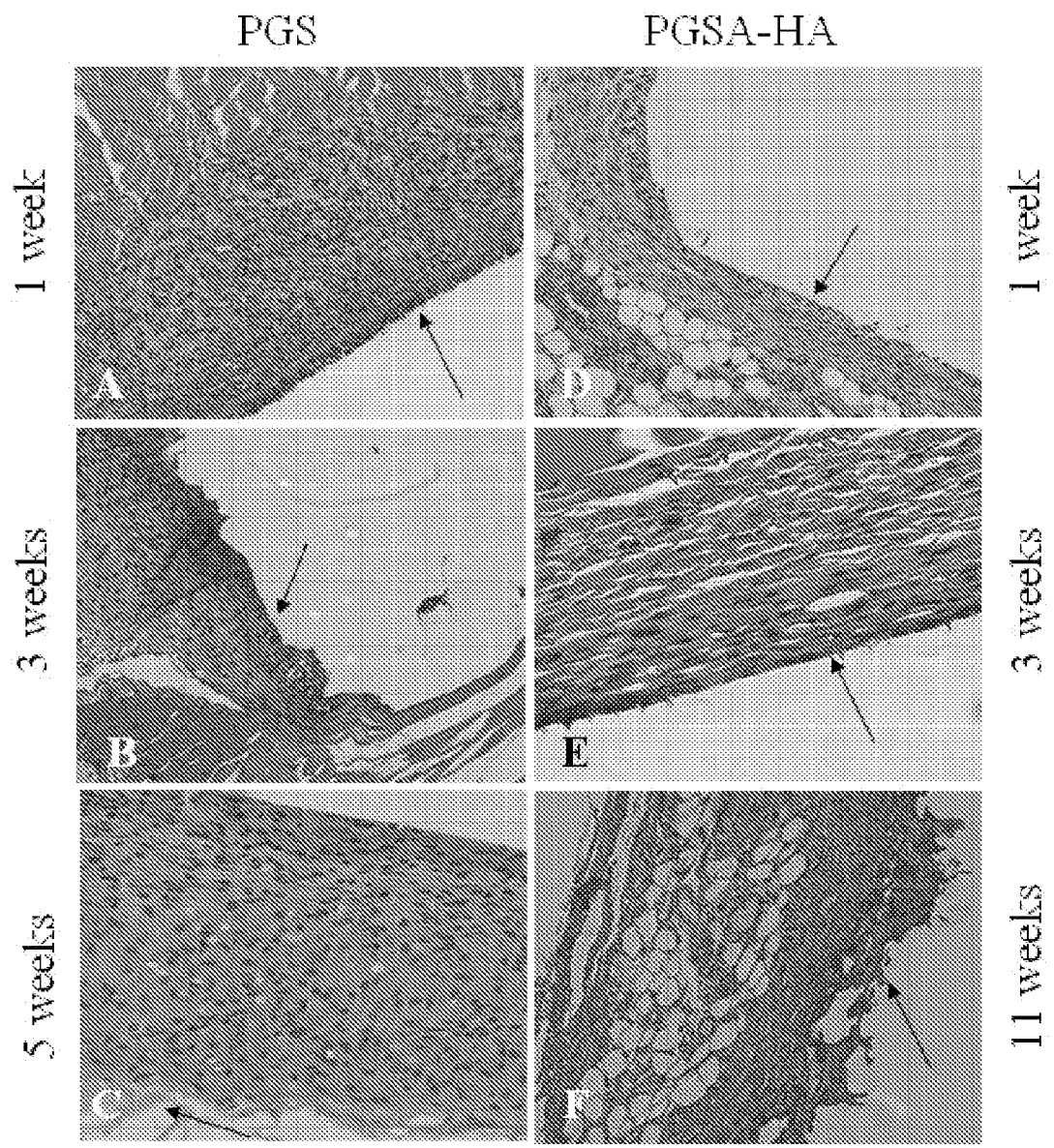
FIGURES 20A-F

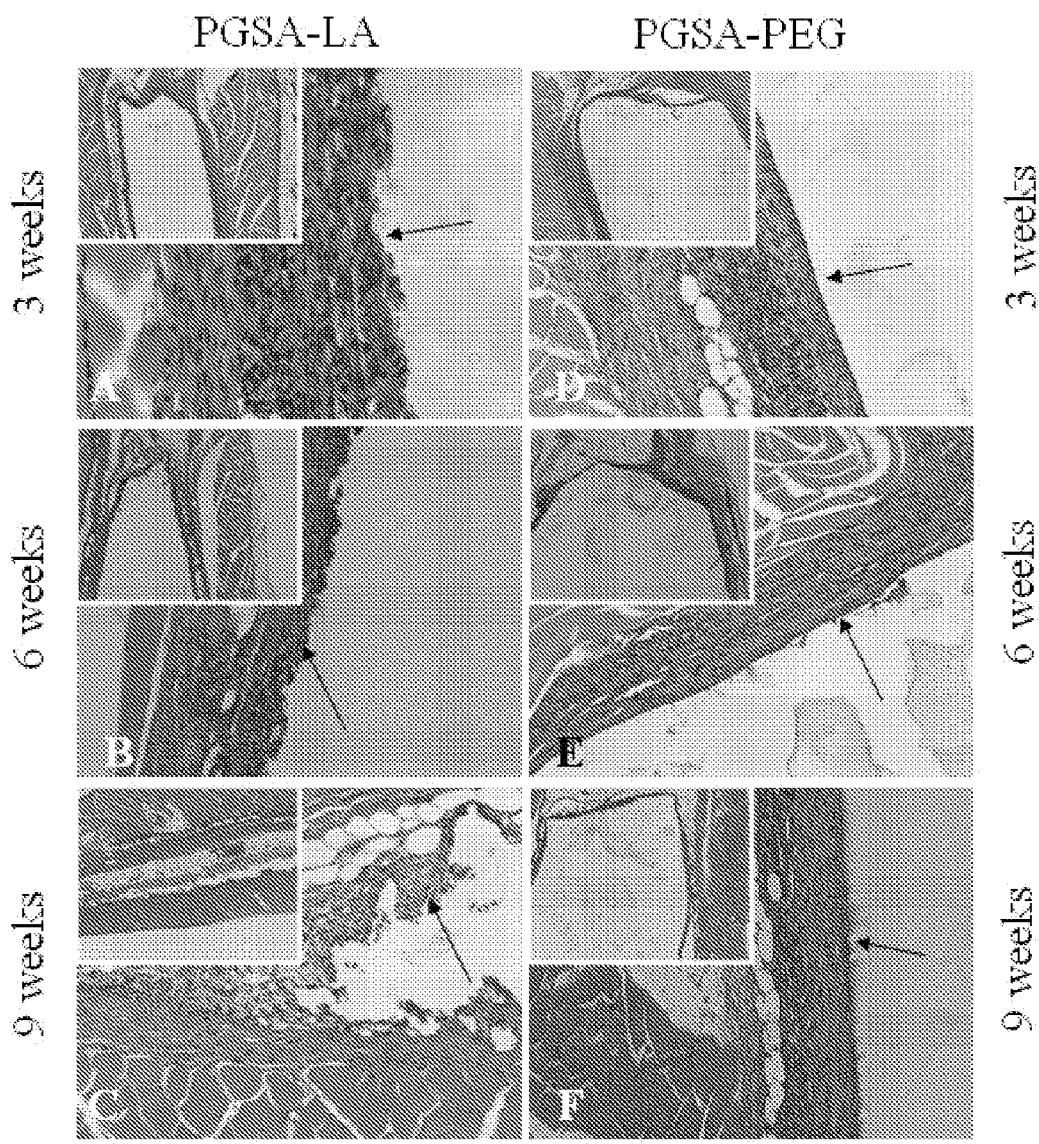
FIGURES 21A-F

US 8,691,203 B2

METHOD COMPRISING CONTACTING TISSUE WITH A CROSS-LINKABLE POLYESTER PREPOLYMER

CROSS-REFERENCE TO RELATED APPLICATIONS

This application is a continuation of prior application U.S. Ser. No. 11/623,041 filed Jan. 12, 2007, now U.S. Pat. No. 8,143,042, entitled "BIODEGRADABLE ELASTOMERS", by Christopher J. Bettinger, which claims priority to U.S. provisional application Nos. 60/758,973 filed Jan. 12, 2006, and 60/803,223 filed May 25, 2006, all of which are herein incorporated by reference in their entirety.

GOVERNMENT SUPPORT

The United States Government has provided grant support utilized in the development of one or more of the present inventions. In particular, National Institute of Health (NIH) contract number DE 013023 and National Science Foundation (NSF) contract number NIRT 0609182 have supported development of one or more of the inventions of the present application. The United States Government may have certain rights in these inventions.

BACKGROUND

Biodegradable polymers are essential materials for a wide variety of biomedical applications including tissue engineering where cell seeded constructs are designed to replace damaged or diseased tissue. These constructs often must provide stability and structural integrity within a mechanically dynamic environment without irritation to the host. Consequently, there is a considerable need and interest in developing tough biodegradable elastomers which exhibit mechanical properties similar to those of soft tissue. Common biodegradable elastomers include, poly(glycerol sebacate), poly(citric diol), star-poly(s-caprolactone-co-D,L-lactide), poly(tri-methylene carbonate-co-s-caprolactone) and poly (tri-methylene carbonate-co-D,L-lactide).

These elastomers, however, have mechanical properties, e.g., as reflected in their elongation % and Young's modulus, that can render them insufficient for many biomedical applications if their biodegradability is to be maintained. For example, as mechanical strength is often proportional to polymer crosslink density, whereas degradability is often inversely proportional to crosslink density, providing a material with both acceptable mechanical strength and degradability is difficult.

Further, these biodegradable elastomers often must be cured at high temperatures in vacuo for extended periods of time (e.g., 24 h) to produce materials with acceptable mechanical properties. This, however, can preclude their use in applications where incorporation of a temperature sensitive component, e.g., a drug, growth factors, cells, etc. is desired. In addition, polymer transitions through a melt phase upon high temperature curing and can produce bubbles which limit the complexity of shapes that can be achieved.

SUMMARY OF THE INVENTION

In various aspects, the present inventions provide elastomeric polymer compositions and methods for their formation and use. In various aspects, the present inventions provide implants and methods of making such implants using various embodiments of the elastomeric polymer compositions of the present inventions. Further aspects and uses of the present inventions are described below.

The compositions and materials of the present inventions provide a biodegradable elastomer, which, in various embodiments, has in vitro and in viva biocompatibility. In addition, in various embodiments the present inventions provide provided methods for adjusting the physical and chemical properties of the resultant composition, and thus the ability to "tailor" a composition. Compositions. For example, in various embodiments and compositions, e.g., one or more of the tensile strength, degradation and swelling properties of the elastomers can be adjusted by varying the density of acrylate moieties in the matrix of the polymer, by incorporation of a hydrogel both.

In various embodiments, the compositions and materials of the present inventions can be formed from a relatively inexpensive biodegradable photocurable elastomer, poly(glycerol sebacate apidicate) PGSA. In various embodiments, the compositions and materials of the present inventions can be formed in seconds via photopolymerization, facilitating, e.g., their formation in situ. In various embodiments, compositions and materials of the present inventions are formed from viscous liquid acrylated pre-polymer, facilitating the molding and/or injection of the acrylated pre-polymer to form materials, structures and various devices. In addition, in various embodiments, the photoinitiated crosslinking reaction used to form the compositions and materials of the present invention, does not require a solvent.

In various aspects, the present inventions provide elastomeric compositions comprising a cross-linked polyester; the cross-linked polyester comprising a polymeric unit of the general formula $(-A-B-)_n$ where, n represents an integer greater than 1, A represents a substituted or unsubstituted ester and B represents a substituted or unsubstituted acid ester comprising at least two acid ester functionalities. At least a portion of the cross-links between polymeric units forming a dioic acid ester between the A components.

Referring to FIG. 1, various embodiments of an elastomeric composition a which comprises a repeating polymeric unit of the general formula $(-A-B-)_n$ are illustrated; the A component including a substituted or unsubstituted ester (102), the B component including a substituted or unsubstituted acid ester comprising at least two acid ester functionalities (104), and the cross-link forming a dioic acid ester (106) between at least a portion of the A components (102).

In various embodiments, these elastomeric compositions comprise a portion that can be represented by the general formula (I) below, where m, n, p, q, and v are each independently integers greater than 1.

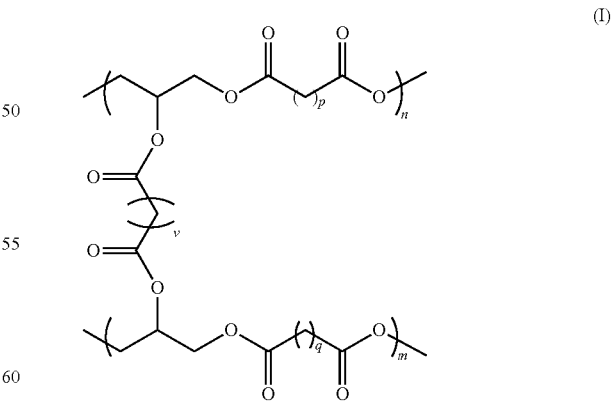

(I)

In various preferred embodiments, an elastomeric composition represented by general formula (I) is derived from cross-linking poly(glycerol sebacate)-acrylate (PGSA) using UV excitation in the presence of a photoiniator (or other free radical initiated systems) of the acrylate to initiate the cross-linking reaction. In various embodiments of the methods of the present invention, one or more hydrogel or other polymeric precursors (e.g., precursors that may be modified to contain acrylate groups such as poly(ethylene glycol), dextran, chitosan, hyaluronic acid, alginate, other acrylate based presursors including, for example, acrylic acid, butyl acrylate, 2-ethylhexyl acrylate, methyl acrylate, ethyl acrylate, acrylonitrile, n-butanol, methyl methacrylate, and TMPTA, trimethylol propane trimethacrylate, pentaerythritol trimethacrylate, pentaerythritol tetramethacrylate, ethylene glycol dimethacrylate, dipentaerythritol penta acrylate, Bis-GMA (Bis phenol A glycidal methacrylate) and TEGDMA (tri-ethylene, glycol dimethacrylate), sucrose acrylate, and combinations thereof, can be reacted with the acrylated prepolymer (e.g., PGSA) prior to or during free radical polymerization to modify the cross-links between the polymer chains.

In various aspects, the present inventions provide elastomeric compositions comprising a cross-linked polyester; the cross-linked polyester comprising a polymeric unit of the general formula $(\text{-A-B-})_n$ cross-linked between at least a portion of the A components of the polyester, the cross-link forming a link comprising at least a portion of the general formula $-(D)_k-C-$; where A represents a substituted or unsubstituted ester, B represents a substituted or unsubstituted acid ester comprising at least two acid ester functionalities; C represents a substituted or unsubstituted dioic acid ester; D represents one or more of a substituted or unsubstituted ester, and k is an integer greater than 0 and and n an integer greater than 1, It is to be understood that the elastomeric compositions can contain one or more kinds of cross-links in addition to a cross-link comprising a dioic acid ester and an ester.

Referring to FIG. 2, various embodiments of an elastomeric composition comprising a repeating polymeric unit of the general formula $(\text{-A-B-})_n$ are illustrated; the A component including a substituted or unsubstituted ester (202), the B component including a substituted or unsubstituted acid ester comprising at least two acid ester functionalities (204), and the cross-link forming a substituted or unsubstituted dioic acid ester (206) and a substituted or unsubstituted ester (208) between at least a portion of the A components (202). In various embodiments, the ester linkage forms a polyester, e.g., p in FIG. 2 is an integer greater than 1.

In various embodiments, these elastomeric compositions comprise a portion that can be represented by the general formula (II) below, where k, m, n, p, q, and v are each independently an integer greater than 1.

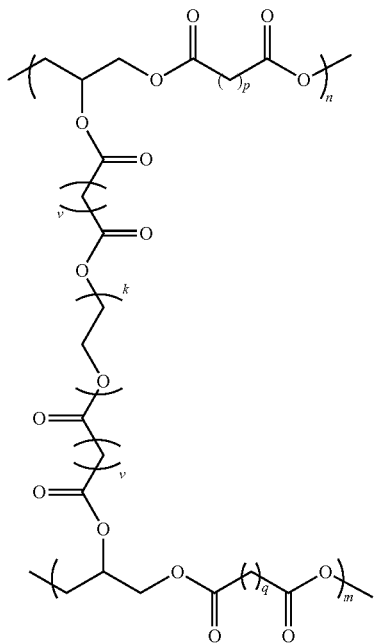

(II)

In various preferred embodiments, an elastomeric composition represented by general formula (II) is derived from copolymerization of PGSA with various proportions of an acrylated polyester, e.g., PEGD, to form one or more crosslinks of the general formula $-(D)_k-C-$; where C represents a dioic acid ester, D represents an ester, and k an integer greater than 1, between polymer chains. In various embodiments, by selecting the proportion of PEGD to PGSA the material properties of the elastomeric composition can be selected. For example, in various embodiments, the PGSA-PEG composition can provide a hydrogel material (e.g., equilibrium water content greater than about 30%) with elastic properties.

In various embodiments, the present inventions provide an elastomeric biodegradable material formed from a cross-linked polyester, the elastomeric biodegradable material having a degradation rate that is substantially non-monotonic as a function of overall cross-link density. In various embodiments the degradation rate is the in vitro degradation rate in phosphate buffer saline (PBS), or in acidic or alkaline conditions. In various embodiments the degradation rate is the in vivo degradation rate. In various embodiments, the present inventions provide an elastomeric biodegradable material formed from a cross-linked polyester, the elastomeric biodegradable material having a degradation rate that is capable of being increased by increasing overall cross-link density. In various embodiments, the present inventions provide an elastomeric biodegradable material formed from a cross-linked polyester, the elastomeric biodegradable material having a degradation rate that is capable of being increased without substantially decreasing the tensile Young's modulus of the material.

In various aspects, the present inventions provide methods for forming a biodegradable elastomeric material, comprising the steps of: (a) reacting a first component comprising two or more functionalities of the general formula —OR, where R of each group is independently hydrogen or alkyl, with a second component comprising two or more acid ester functionalities to form a mixture of pre-polymers having a molecular weight in the range between about 300 Da and about 75,000 Da; (b) reacting the mixture of pre-polymers with an acrylate to form a mixture of acrylated pre-polymers; and (c) irradiating the acrylated pre-polymer mixture with ultraviolet light to cross-link at least a portion of the acrylated pre-polymers and form a biodegradable elastomeric material; wherein the pre-polymer mixture is not heated above about 45° C. during irradiation, and preferably not above about 37° C., and more preferably not above about 25° C.

In various embodiments, the methods comprise adding one or more additional acrylated molecules (referred to as acrylated co-polymers herein) during the reacting the mixture of pre-polymers with an acrylate, or to the mixture of acrylated pre-polymers. A wide variety of co-polymers can be used including, but not limited to, dextran, hyaluronic acid, chitosan, and poly(ethylene glycol).

In various aspects, the present inventions provide methods for forming a biodegradable elastomeric material, comprising the steps of (a) providing a solution comprising: a prepolymer comprising (i) a first component comprising two or more functionalities of the general formula —OR, where R of each group is independently hydrogen or alkyl; and (ii) a second component comprising two or more acid ester functionalities; and (c) crosslinking at least a portion of the pre-polymers using one or more of a Mitsunobu-type reaction, polymerization using a thermal initiator, redox-pair initiated polymerization, and a Michael-type addition reaction using a bifunctional sulfhydryl compound.

The compositions and materials of the present inventions are suitable for a wide range of uses. In various embodiments, the chemical and mechanical properties of these materials and compositions (and the ability to adjust them) make them attractive candidates for elastomers could find utility for treating cardiovascular disease, for bridging neural defects where existing graft materials have severe limitations.

For example, it has been reported that the peripheral nerve has a Young's modulus of approximately 0.45 MPa and the thoracic aorta has a Young's modulus of 0.53 MPa. In various embodiments, the present invention provides compositions and materials that can achieve mechanical compliance with such biological structures. In addition, in various embodiments, the present inventions provide compositions and materials where, e.g., the swelling and/or degradation of the composition or material can be adjusted without substantially changing the Young's modulus.

Various embodiments of the compositions and materials of the present inventions, can be used in a variety of medical applications, including, but not limited to, bioactive agent delivery vehicles (e.g., delivery of antibiotics, drugs, etc), patches for diabetic ulcers, abdominal implant to prevent adhesions, biodegradable adhesive, in vivo and in vitro sensors, catheters, surgical glue, cardiac, bile-duct, intestinal stent, coatings for metals, microfabrication applications (e.g., capillary networks), long-term circulating particles for applications including targeted drug delivery, blood substitutes etc., injectable drug delivery system for mechanically taxing environments (e.g., within joints) where, for example, the material can be configured to release drags in controlled manner without being compromised by a dynamic or static external environment, degradable O-rings, septums etc.

Various embodiments of the compositions and materials of the present, can be used in a variety of non-medical applications, including, but not limited to, an absorbent garments, (e.g., disposable diapers, incontinence protectors, panty liners, sanitary napkins, etc.), chewing gum (e.g., to deliver nutrients), inflatable balloons, fishing lures, fishing flies, disposable bags, edible films (e.g., films that protect the freshness of food product but that are biodegradable within the digestive tract), degradable films (alternative to saran wrap/cellophane), general packaging (e.g., degradable in composts or landfills), flavor and aroma barriers, food containers, degradable foams for packaging applications, degradable filters, hair products (e.g., as alternatives to existing wax products), agricultural seeding strips and tapes, cosmetics, preservation of materials (e.g. wood), limited and/or one time-use CDs, DVDs etc. (e.g., that can be written but not copied).

In various embodiments, the present inventions provide an elastic biodegradable material formed from a cross-linked polyester composition of the present inventions, wherein the elastic biodegradable material is in the form of a particle, tube, sphere, strand, coiled strand, capillary network, film, fiber, mesh, or sheet.

In various embodiments, the present inventions provide medical device formed from an elastic biodegradable material of the present inventions. In various embodiments, the medical device provides delivery of a bioactive agent over time. In various embodiments, the medical device is implanted and/or formed in situ. For example, in various embodiments, the medical device is formed by injecting an acrylated pre-polymer of the present inventions at a site where the medical device is desired; and irradiating the injected acrylated pre-polymer with ultraviolet light to form the medical device. In various embodiments, the medical device comprises a graft and/or implant to facilitate tissue repair and/or regeneration.

In various embodiments, is provided an elastomeric biodegradable material formed from a cross-linked polyester of the present inventions, where the material comprises one or more of a growth factor, cell adhesion sequence, polynucleotide, polysaccharide, polypeptide, an extracellular matrix component, and combinations thereof. In various embodiments, is provided an elastomeric biodegradable material formed from a cross-linked polyester of the present inventions, where the material is seeded with one or more connective tissue cells, organ cells, muscle cells, nerve cells, and combinations thereof. In various embodiments, is provided an elastomeric biodegradable material formed from a cross-linked polyester of the present inventions, where the material is seeded with one or more tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, and bone-forming cells.

The foregoing and other aspects, embodiments, and features of the present inventions can be more fully understood from the following description and drawings.

BRIEF DESCRIPTION OF THE DRAWINGS

FIGS. 3A-D schematically illustrates a formation scheme for an elastomeric composition or material according to various embodiments of the present inventions. FIG. 3A illustrating polycondensation of glycerol and sebacic acid, to form a pre-polymer (a low molecular weight polymer is illustrated), where R is H, and alkyl, alkenyl, or alkynyl). FIG. 3B illustrating functionalization of the pre-polymer backbone with a vinyl group, here acrylation is shown. FIGS. 3C and 3D schematically illustrate examples of portions of the polymer network formed in a various embodiments of a cross-linked polymer of PGSA FIG. 4 schematically illustrates an example of the portion of the polymer network formed in a various embodiments of a cross-linked, polymer of PGSA-PEG.

FIG. 5A illustrating adjustments for a PGSA-PEG and FIG. 5B for a PGSA-Dextran co-polymer.

FIG. 7A-D illustrates that the elastomeric compositions of various embodiments of the present invention can be fabricated into a wide variety of shapes and morphologies including: (FIG. 7A) nano/microparticles; (FIG. 7B) tubes, (FIG. 7C) micropatterns, and (FIG. 7D) scaffolds.

FIG. 8A showing a spectrum of PGS pre-polymer and FIG. 8B of PGSA.

FIGS. 9A and 9B compare ATR-FTIR spectra of PGS pre-polymer PGS pre-polymer (902); PGSA with a DA of 0.20 (904); PGSA (DA=0.54) (906); thermally cured PGS (908); photocured PGSA (DA=0.20) (910); and photocured PGSA (DA=0.54) (912).

FIG. 11A presents data on the tensile strength and elongation, FIG. 11B presents data on Young's modulus and ultimate strength; and FIG. 11C presents data on swelling in ethanol, selling in water, and sol content.

FIGS. 14A-C present in vitro cell attachment and degradation data; FIGS. 14A and 14B are SEM pictures of the surface of photocured PGSA (DA=0.31) (PGSA-LA) after 3 hours in 0.1 mM NaOH at 37° C., and after 12 days, respectively. FIG. 14C is a plot of cell density over time on photocured PGSA surfaces.

FIG. 16A changes in mass; FIG. 16B water content; FIG. 16C sol content; FIG. 16D size of PGS, PGSA-LA, PGSA-HA, PGSA-PEG implants after in vivo degradation. PGS and PGSA-LA were fully degraded at implantation site after, respectively, 7 and 12 weeks in viva (n=4).

FIGS. 18A-H present SEM cross-sectional images of polymeric discs, as further described in Example 2, of (FIGS. 18A and E) PGS at 3 and 5 weeks in vivo, (FIGS. 18B and F) PGSA-LA at 3 and 9 weeks in viva, (FIGS. 18C and G) PGSA-HA at 3 and 11 weeks in vivo and (FIGS. 18D and H) PGSA-PEG at 3 and 9 weeks in vivo (n=4).

FIGS. 19A-D present surface SEM images of polymeric discs, as further described in Example 2, of (FIG. 19A) PGS at 5 weeks in vivo, (FIG. 19B) PGSA-LA at 6 weeks in vivo, (FIG. 19C) PGSA-HA at 5 weeks in vivo and (FIG. 19D) PGSA-PEG at 6 weeks in viva (n=4).

FIGS. 20A-F present photomicrographs (400×) of H&E sections of tissue adjacent elastomeric implants, as further described in Example 2, of the tissue reaction of: (FIGS. 20A and C) PGS (positive control) after 1, 3 and 5 weeks in vivo and (FIGS. 20D-F) PGSA-HA after 1, 3 and 11 weeks in vivo (n=4). Arrows indicate polymer-tissue interface surface.

FIGS. 21A-F present photomicrographs (400×), and in figure inset (50×) of H&E sections of tissue adjacent elastomeric implants, as further described in Example 2, of the tissue reaction of (FIGS. 21A-C) PGS-LA after 3, 6 and 6 weeks in vivo and (FIGS. 21D-F) PGSA-HA after 3, 6 and 9 weeks in vivo (n=4). Arrows indicate polymer-tissue interface surface.

DETAILED DESCRIPTION OF VARIOUS EMBODIMENTS

Figure 1:
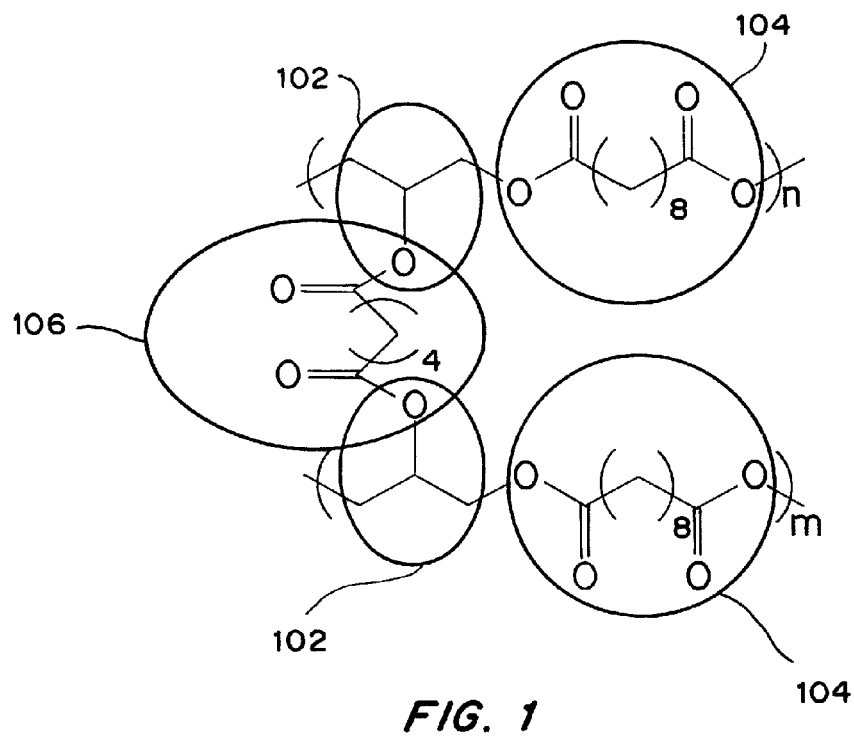
FIG. 1 schematically illustrates various embodiments of an elastomeric composition of the present inventions.
Figure 2:
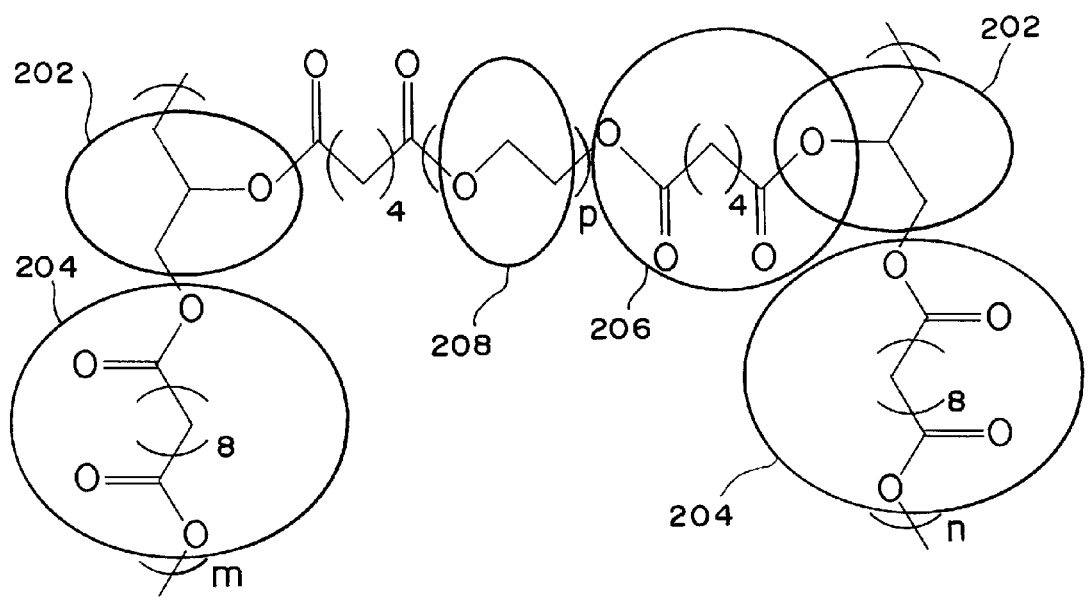
FIG. 2 schematically illustrates various embodiments of an elastomeric composition of the present inventions.

Prior to further describing the present inventions, it may be helpful to provide an understanding thereof to set forth the meanings of certain terms to be used herein.

As used herein, the article "a" is used in its indefinite sense to mean "one or more" or "at least one." That is, reference to any element of the present teachings by the indefinite article "a" does not exclude the possibility that more than one of the element is present.

The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

The term "biocompatible", as used herein is intended to describe materials that do not elicit a substantial detrimental response in vivo.

As used herein, "biodegradable" polymers are polymers that degrade down to monomeric species under physiological or endosomal conditions. In various preferred embodiments, the polymers and polymer biodegradation byproducts are biocompatible. Biodegradable polymers are not necessarily hydrolytically degradable and may require enzymatic action to fully degrade.

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

The terms "polynucleotide", "nucleic acid", or "oligonucleotide" refer to a polymer of nucleotides, The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2″-fluororibose, ribose, 2'-deoxyribose, arabinose, and hexose), or modified phosphate groups (e.g., phosphorothioates and 5'-N-phosphoramidite linkages).

As used herein, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco-.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2"-deoxyribose, and hexose).

As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. In certain embodiments, the bioactive agent is a drug.

A more complete listing of examples of bioactive agents and specific drugs suitable for use in the present invention may be found in "Pharmaceutical Substances: Syntheses, Patents, Applications" by Axel Kleemamm and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmacopeial Convention, Inc., Rockville Md., 2001, the entire contents of which are herein incorporated by reference.

As used herein, the term "tissue" refers to a collection of similar cells combined to perform a specific function, and any extracellular matrix surrounding the cells.

The term "substituted" is intended to describe groups having substituents replacing a hydrogen on one or more atoms, e.g., carbon, nitrogen, oxygen, etc., of a molecule. Substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, infirm, sulfhydryl, alkylthio, arylthio, nitro, trifluoromethyl, cyano, azido, heterocyclyl, alkylaryl, or an aromatic or heteroaromatic group. Accordingly, the phrase "a substituent as described herein" or the like refers to one or more of the above substituents, and combinations thereof.

The term "alkyl" includes saturated aliphatic groups, which includes both "unsubstituted alkyls" and "substituted alkyls", the latter of which refers to alkyl groups having substituents replacing a hydrogen on one or more carbons of the hydrocarbon backbone. The term "alkyl" includes straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), and cycloalkyl substituted alkyl groups, The term "alkyl" also includes the side chains of natural and unnatural amino acids.

An "alkylaryl" or an "aralkyl" group is an alkyl substituted with an aryl (e.g., phenylmethyl (benzyl)).

The term "aryl" includes 5- and 6-membered single-ring aromatic groups, as well as multicyclic aryl groups, e.g., tricyclic, bicyclic, e.g., naphthalene, anthracene, phenanthrene, etc.). The aromatic ring(s) can be substituted at one or more ring positions with such substituents as described above. Aryl groups can also be fused or bridged with, e.g., alicyclic or heterocyclic rings which are not aromatic so as to form, e.g., a polycycle.

The term "alkenyl" includes unsaturated aliphatic groups analogous in length and possible substitution to the alkyls described above, but which contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (angelic) groups (cyclopropenyl, cyclopentenyl, cyolohexenyl, cycloheptenyl, cyclooctenyl), alkyl or alkenyl substituted cycloalkenyl groups, and cycloalkyl or cycloalkenyl substituted alkenyl groups. The term alkenyl includes both "unsubstituted alkenyls" and "substituted alkenyls", the latter of which refers to alkenyl groups having substituents replacing a hydrogen on one or more carbons of the hydrocarbon backbone.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butyryl, pentynyl, hexynyl, heptynyl, octenyl, nonynyl, decynyl, etc.), branched-chain alkynyl groups, and cycloalkyl or cycloalkenyl substituted alkynyl groups. The term alkynyl includes both "unsubstituted alkynyls" and "substituted alkynyls", the latter of which refers to alkynyl groups having substituents replacing a hydrogen on one or more carbons of the hydrocarbon backbone.

The term "acyl" includes compounds and groups which contain the acyl radical ($CH_3CO-$) or a carbonyl group. The term "substituted acyl" includes acyl groups having substituents replacing a one or more of the hydrogen atoms.

The term "acylamino" includes groups wherein an acyl group is bonded to an amino group. For example, the term includes alkylcarbonylamino, arylcarbonylamino, carbamoyl and ureido groups.

The term "aroyl" includes compounds and groups with an aryl or heteroaromatic group bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "acylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or groups that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl groups bound to an amino group which is bound to the carbon of a carbonyl or thiocarbonyl group. The terms "alkylaminocarboxy," "alkenylaminocarboxy," "alkynylaminocarboxy," and "arylaminocarboxy" include groups wherein alkyl, alkenyl, alkynyl and aryl groups, respectively, are bound to a nitrogen atom which is in turn bound to the carbon of a carbonyl group.

The term "carbonyl" or "carboxy" includes compounds and groups which contain a carbon connected with a double bond to an oxygen atom, and tautomeric forms thereof. Examples of groups that contain a carbonyl include aldehydes, ketones, carboxylic acids, amides, esters, anhydrides, etc. The term "carboxy group" or "carbonyl group" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl group. For example, the term includes groups such as, for example, aminocarbonyl groups, (wherein a nitrogen atom is bound to the carbon of the carbonyl group, e.g., an amide), aminocarbonyloxy groups, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. groups.

The term "ether" includes compounds or groups that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and groups that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O$^-$.

The term "halogen" includes fluorine, bromine, chlorine, iodine, etc. The term "perhalogenated" generally refers to a group wherein all hydrogens are replaced by halogen atoms.

The term "heteroatom" includes atoms of any element other than carbon or hydrogen. Preferred heteroatoms are nitrogen, and oxygen. The term "heterocycle" or "heterocyclic" includes saturated, unsaturated, aromatic ("heteroaryls" or "heteroaromatic") and polycyclic rings which contain one or more heteroatoms. The heterocyclic may be substituted or unsubstituted. Examples of heterocyclics include, for example, benzodioxazole, benzofuran, benzoimidazole, benzothiazole, benzothiophene, benzoxazole, chromene, deazapurine, furan, indole, indolizine, imidazole, isoxazole, isoindole, isoquinoline, isothiaozole, methylenedioxyphenyl, napthridine, oxazole, purine, pyran, pyrazine, pyrazole, pyridazine, pyridine, pyrimidine, pyrrole, quinoline, tetrazole, thiazole, thiophene, and triazole. Other heterocycles include morpholino, piprazine, piperidine, thiomorpholino, and thioazolidine.

The terms "polycyclic ring" and "polycyclic ring structure" include groups with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic ring can be substituted with such substituents as described above.

In various aspects, the present inventions provide elastic biodegradable polymer compositions and materials formed by the reaction of a multifunctional alcohol or ether (that is a compound having two or more OR groups, where each R is independently H and an alkyl) and a difunctional or higher order acid (e.g., a diacid) to form a pre-polymer (see, e.g., FIG. 3A), which is cross-linked to form the elastic biodegradable polymer. In preferred embodiments, the cross-linking is performed by functionalization of one or more OR groups on the pre-polymer backbone with vinyl (see, e.g., FIG. 3B), followed by photopolymerization to form the elastic biodegradable polymer composition or material. Preferably, acrylate is used to add one or more vinyls to the backbone of the pre-polymer to form an acrylated pre-polymer.

Referring to FIGS. 3A-D and 4, this formation scheme is schematically illustrated. It is to be understood that the acrylation and polymerization reactions can result in several types of cross-links within the polymer network. For example, the acrylated hydroxyl upon photopolymerization can yield acid ester cross-links to an alkyl chain (also know in the art as a methylene chain) (see, e.g., FIG. 3C), as well as dioic acid ester cross-links when, for example, two acrylated hydroxides react (see, e.g., FIG. 3D.)

Diacid Component

A wide variety of diacid, or higher order acids, can be used in the formation of a elastic biodegradable polymer compositions and materials according to various embodiments of the present invention, including, but are not limited to, glutaric acid (5 carbons), adipic acid (6 carbons), pimelic acid (7 carbons), suberic acid (8 carbons), and azelaic acid (nine carbons). Exemplary long chain diacids include diacids having more than 10, more than 15, more than 20, and more than 25 carbon atoms. Non-aliphatic diacids can be used. For example, versions of the above diacids having one or more double bonds can be employed to produce glycerol-diacid co-polymers. Amines and aromatic groups can be incorporated into the carbon chain. Exemplary aromatic diacids include terephthalic acid and carboxyphenoxypropane. The diacids can also include substituents as well. For example, in various embodiments, reactive groups like amine and hydroxyl can be used increase the number of sites available for cross-linking. In various embodiments, amino acids and other biomolecules can be used to modify the biological properties of the polymer. In various embodiments, aromatic groups, aliphatic groups, and halogen atoms can be used to modify the inter-chain interactions within the polymer.

Pre-Polymer

In various embodiments, the pre-polymer of the present inventions comprises a diol, or higher order, portion and a diacid, or higher order acid, portion. In various embodiments, the pre-polymer can include unsaturated diols, e.g., tetradeca-2,12-diene-1,14-diol, or other diols including macromonomer diols such as, e.g., polyethylene oxide, and N-methyldiethanoamine (MDEA). In addition to incorporating these into the pre-polymer, the diols can be incorporated into the resultant cross-linked polymer through, e.g., acrylate chemistry. For example, the diols could be first acrylated and then combined with acrylated pre-polymer using a free radical polymerization reaction. In various embodiments, aldehydes and thiols can be used, e.g., for attaching proteins and growth factors to the pre-polymer.

Vinyl Addition to Pre-Polymer

A variety of techniques can be used to functionalize the pre-polymer with vinyl. In various preferred embodiment an acrylate, such as, for example, an acrylate monomer. Examples of suitable acrylate monomers include, but are not limited to, methacrylate, vinyl methacrylate, maleic methacrylate, and those having the structure

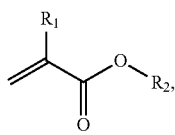

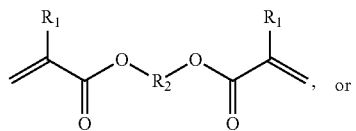, or

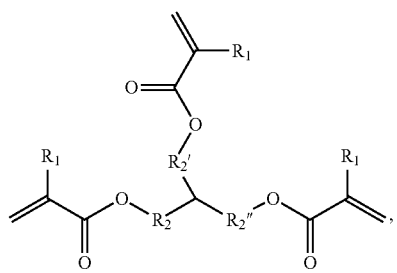

where $R_1$ can be methyl or hydrogen; and $R_2$, $R_2'$, and $R_2''$ can be alkyl, aryl, heterocycles, cycloalkyl, aromatic heterocycles, multicycloalkyl, hydroxyl, ester, ether, halide, carboxylic acid, amino, alkylamino, dialkylamino, trialkylamino, amido, carbamoyl thioether, thiol, alkoxy, or ureido groups. $R_2$, $R_2'$, and $R_2''$ may also include branches or substituents including alkyl, aryl, heterocycles, cycloalkyl, aromatic heterocycles, multicycloalkyl, hydroxyl, ester, ether, halide, carboxylic acid, amino, alkylamino, dialkylamino, trialkylamino, amido, carbamoyl, thioether, thiol, alkoxy, or ureido groups. Further examples of suitable acrylate monomers include, but are not limited, to,

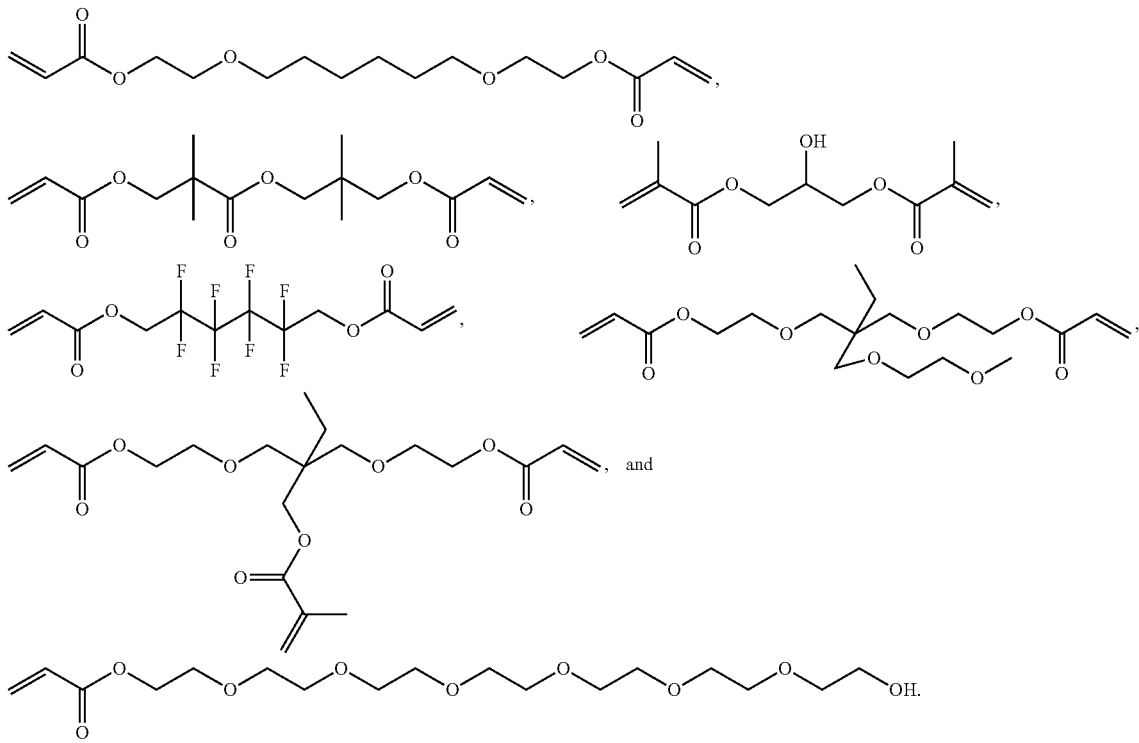

In addition to acrylate monomers, other agents can be used to form a functionalized pre-polymer that can be cross-linked by photopolymerization in accordance with various embodiments of the present inventions. Examples of such agents include, but are not limited to, glycidyl, epichlorohydrin, triphenylphosphine, diethyl azodicarboxylate (DEAD), divinyladipate, and divinylsebacate with the use of enzymes as catalysts, phosgene-type reagents, di-acid chlorides, bis-anhydrides, bis-halides, metal surfaces, and combinations thereof.

It is to be understood that, in various embodiments, vinyl groups can be incorporated in the backbone of the pre-polymer using, e.g., free carboxyl groups on the pre-polymer. For example, hydroxyethyl methacrylate can be incorporated through the COOH groups of the pre-polymer using carbonyl diimidazole activation chemistry.

Vinyl groups can be incorporated in the backbone of the pre-polymer with or with-out the use of catalyst, although the use of a catalyst is preferred. A wide variety, of catalysts can be used in various embodiments, including, but not limited to, 4-(dimethylamino)pyridine, N-hydroxy succinimide, carbodiimides, and pyridine. Preferably, the reaction is carried out in a solvent, examples of suitable solvents include, but are not limited to, benzene, toluene, chloroform, dichloromethane, ethyl acetate, and tethrahydrofuran.

In various embodiments, acrylation of the pre-polymer can be carried out by reacting the pre polymer with acryloyl chloride (in the presence of triethylamine and 4-(dimethylamino)pyridine (4-DMAP) as catalysts) in anhydrous dichloromethane. Using these reagents it is preferred that that this reaction is carried out under extremely dry conditions. An example of a resultant acrylation is schematically illustrated in FIG. 3B. It is to be understood that not all binding possibilities and resultant products are shown in FIG. 3B. For example, although it is believed that the backbone OH groups of the pre-polymer are preferentially acrylated, the carboxylic acid groups can also be modified.

The degree of acrylation of the pre-polymer can be used to adjust the properties of the resultant cross-linked polymer. Accordingly, in various aspects the present inventions provide methods for formation of elastomeric polymers with specific physical and mechanical properties. In various embodiments, one or more of the degree of acrylation and the use of substituents on the acrylate groups can be used to control properties such as degradation and swelling and mechanical properties.

The molar ratio of acryloyl chloride to available hydroxyl groups can be varied to adjust the degree of acrylation. In various embodiments, the acrylated pre-polymer is a viscous liquid that can be cured without solvent. Accordingly, in various embodiments, the present inventions provide methods for in vivo curing of the acrylated pre-polymer to form a elastomeric biodegradable composition or material.

Photopolymerization and

In various embodiments, the acrylated pre-polymers into a polymeric network using a free radical initiated reaction, such as, for example, by photoinitiated polymerization, photopolymerization. In various preferred embodiments, acrylated pre-polymer is irradiated with light (typically ultraviolet (UV) light) in the presence of a photoinitiator to facilitate the reaction. Examples of suitable photoinitiators include, but are not limited to: 2-dimethoxy-2-phenyl-acetophenone, 2-hydroxy-[4-(hydroxyethoxy)phenyl]-2-methyl-1-propanone (Irgacure 2959), 1-hydroxycyclohexyl-1-phenyl ketone (Irgacure 184), 2-hydroxy-2-methyl-1-phenyl-1-propanone (Darocur 1173), 2-benzyl-2-(dimehylamino)-1-[4-morpholinyl) phenyl]-1-butanone (Irgacure 369), methylbenzoylformate (Darocur MBF), oxy-phenyl-acetic acid-2-[2-oxo-2-phenyl-acetoxy-ethoxy]-ethyl ester (Irgacure 754), 2-methyl-1-[4-(methylthio)phenyl]-2-(4-morpholinyl)-1-propanone (Irgacure 907), diphenyl(2,4,6-trimethylbenzoyl)-phosphine oxide (Darocur TPO), phosphine oxide, phenyl bis(2,4,6-trimethyl benzoyl) (Irgacure 819), and combinations thereof. In various preferred embodiments, acrylated pre-polymer is irradiated with visible light (typically blue light) in the presence of a photoinitiator to facilitate the reaction. Examples of photoinitiators for visible light include camphorquinone among others.

In various embodiments, e.g., in viva photopolymerization and other medical applications, the use of cytocompatible photoinitiators is preferred and may be require by regulatory agencies. It has been reported that the photoinitiator Irgacure 2959 causes minimal cytotoxicity (cell death) over a broad range of mammalian cell types and species.

Cross-Links and the Polymer Network

Figures 3D, 4:
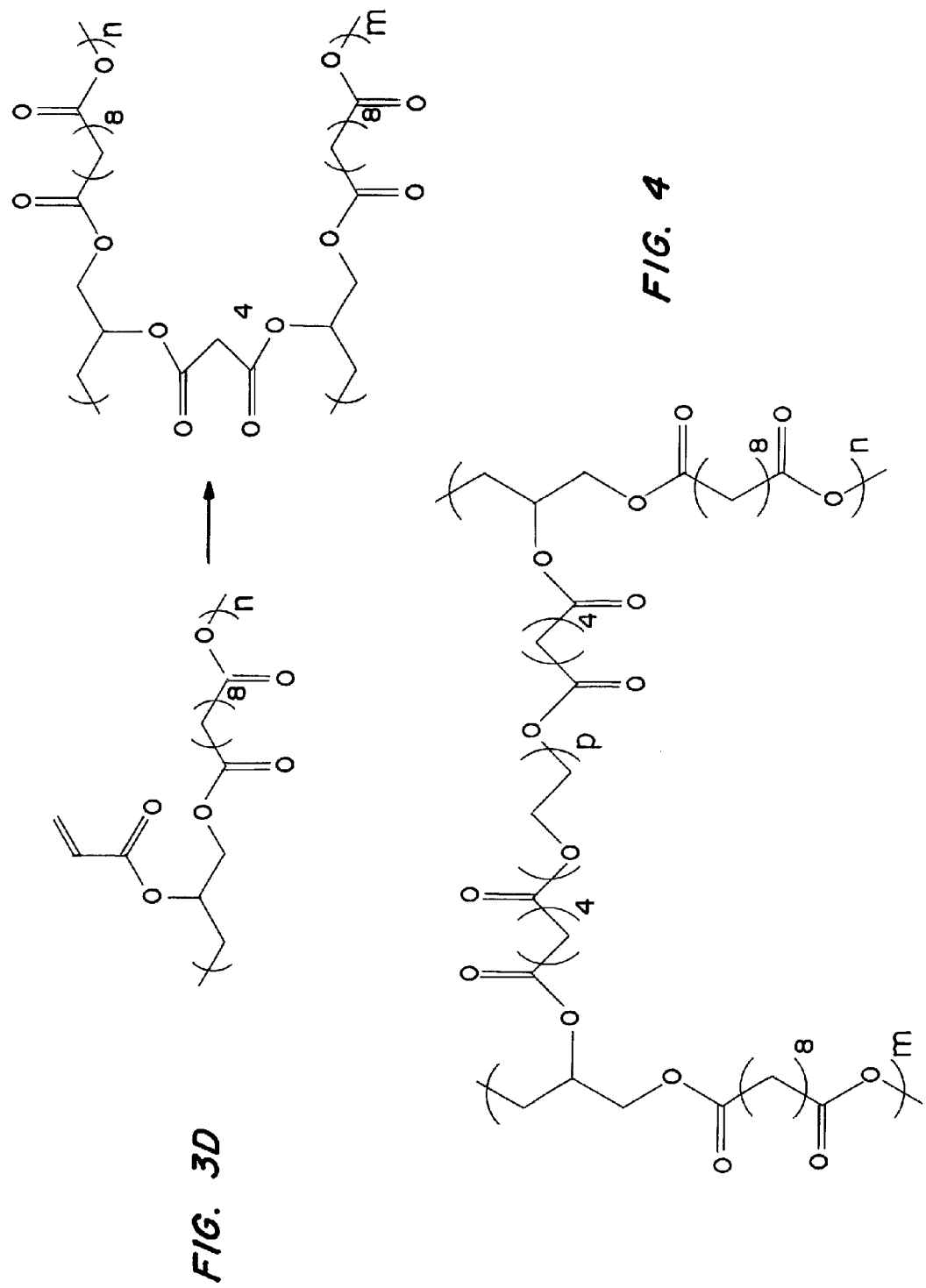

It is to be understood that in the formation of a polymer network that the links and polymer strands of the network are not homogeneous. For example, FIGS. 3C and 3D schematically illustrate examples of portions of the polymer network formed by the photopolymerization methods of the present invention using PGSA.

In various aspects of the present invention, the formation of different cross-links in the polymer network is exploited to adjust, or even "tailor" the properties of the resultant polymer. For example, FIG. 4 schematically illustrate examples of portions of the polymer network formed by the photopolymerization methods of the present invention using PGSA and PEGD, it being understood that cross-links substantially as illustrated in FIGS. 3C and 3D are also present in the PGSA-PEG polymer network, In various embodiments, a biodegradable material formed from the a composition of the present invention not containing a co-polymer, is provided that has one or more of the following properties: (a) a tensile Young's modulus less than about 1.5 MPa when measured according to ASTM standard D412-98a; (b) a tensile Young's modulus greater than about 0.05 MPa and an elongation of greater than about 45%, both when measured according to ASTM standard D412-98a; (c) a Young's modulus in the range between about 0.4 MPa and about 0.55 MPa when measured according to ASTM standard D412-98a; (d) a maximum elongation greater than about 170%; (e) a degree of acrylation in the range between about 0.25 to about 0.35 and a Young's modulus in the range between about 0.3 and 0.5 MPa when measured according to ASTM standard D412-98a; (f) a degree of acrylation in the range between about 0.35 to about 0.45 and a Young's modulus in the range between about 0.7 and 1 MPa when measured according to ASTM standard D412-98a; (g) a degree of acrylation in the range between about 0.25 to about 0.5 and an elongation greater than about 40%.

"Co-Polymer" Networks

In various aspects, the present inventions provide elastic biodegradable polymer compositions and materials formed from an acrylated pre-polymer of the present inventions and one or more additional molecules (referred to as co-polymers herein) functionalized to the acrylate of the acrylated pre-polymer and/or a hydroxyl group of the acrylated pre polymer. A wide variety of co-polymers can be used including, but not limited to, one or more hydrogel or other polymeric precursors (e.g., precursors that may be modified to contain acrylate groups such as poly(ethylene glycol), dextran, chitosan, hyaluronic acid, alginate, acrylate based precursors including, for example, acrylic acid, butyl acrylate, 2-ethylhexyl acrylate, methyl acrylate, ethyl acrylate, acrylonitrile, n-butanol, methyl methacrylate, and TMPTA, trimethylol propane trimethacrylate, pentaerythritol trimethacrylate, pentaerythritol tetramethacrylate, ethylene glycol dimethacrylate, dipentaerythritol penta acrylate, Bis-GMA (Bis phenol A glycidal methacrylate) and TEGDMA (triethylene, glycol dimethacrylate), sucrose acrylate, etc. and combinations thereof, can be reacted with the acrylated pre-polymer (e.g. PGSA) prior to or during free radical polymerization to modify the cross-links between the polymer chains.

In various aspects, the present inventions provide elastic biodegradable polymer compositions and materials formed by the reaction of a multifunctional alcohol or ether (that is a compound having two or more OR groups, where each R is independently H and an alkyl) and a difunctional or higher order acid (e.g., a diacid) to form a pre-polymer (see, e.g., FIG. 3A). In various embodiments, at least a portion of the pre-polymers are functionalized with a vinyl group to form a mixture of acrylated pre-polymers which are reacted with one or more co-polymers to form. It is to be under stood that the co-polymer can be added before acrylation of the pre-polymer, during the acrylation reaction, after to the acrylated pre-polymer, or a combination thereof. The resultant mixture is then photopolymerized to form the polymer network. In various preferred embodiments, the co-polymer is acrylated and the acrylated co-polymer combined with the acrylated pre-polymer. In various embodiments, the acrylation of the co-polymer and/or prepolymer with an assymetrical monoacrylate molecules (e.g. Acryloyl-poly(ethylene glycol)-N-hydroxy succinimide) provides, for example, an anchoring moiety that can be further modified (e.g., addition of cell-adhesive molecules).

In various aspects of the present invention, the formation of different cross-links in the polymer network is exploited to adjust, or even "tailor" the properties of the resultant polymer. For example, in various embodiments two or more types of cross-links (e.g. numbers of carbons, different types of groups, e.g., aromatic groups being more rigid, etc.) are used to adjust the properties of the resultant polymer network. In various embodiments, an acrylated pre-polymer (e.g., PGSA) can be combined with a co-polymer (e.g. PEG) in proportions to provide, e.g., one or more of swelling control, degradation control and anti-fouling of the crosslinked polyester.

Figure 5A:
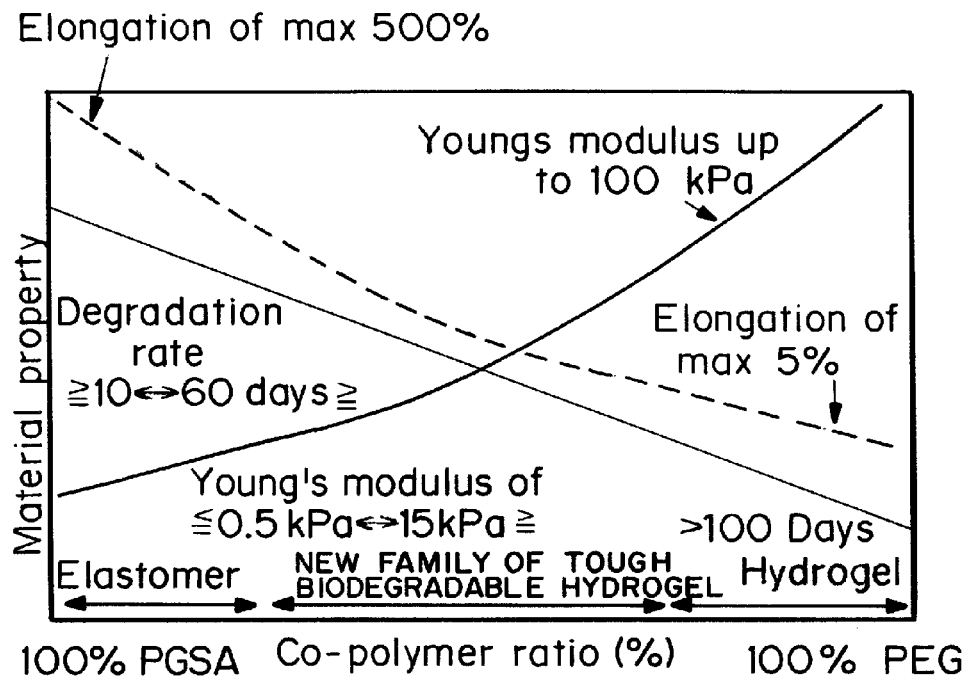
FIG. 5A-B schematically depicts the adjustment of the physical properties of a polymer based on the proportion of PGSA.
Figure 5B:
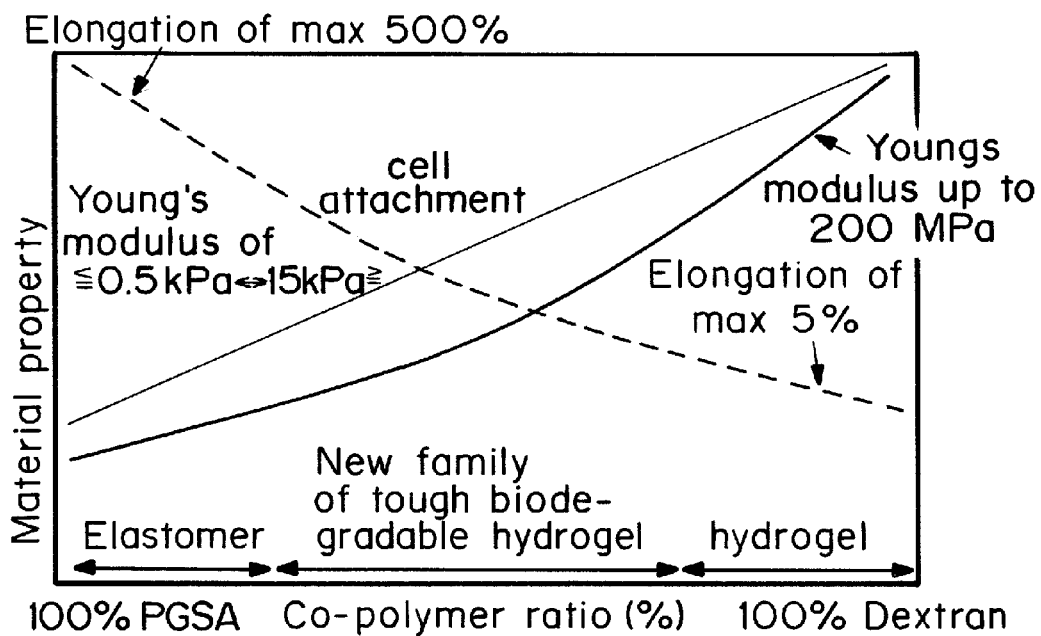

For example, in various embodiments, combining an acrylated pre-polymer with other acrylated co-polymers can be used to obtain degradable materials with properties that span rigid materials to tough degradable elastomers to soft hydrogels. FIGS. 5A and 5B schematically illustrate that range over which various chemical and physical properties can be adjusted by adjusting the ratio of the acrylated pre-polymer and co-polymer in the material. FIG. 5A illustrating the adjustments for a PGSA-PEG composition or material, and FIG. 5B illustrating the adjustments for a PGSA-Dextran. In addition, as discussed herein, further property control can be achieved by adjustment of the DA of the pre-polymer, co-polymer, or both.

Figure 12:
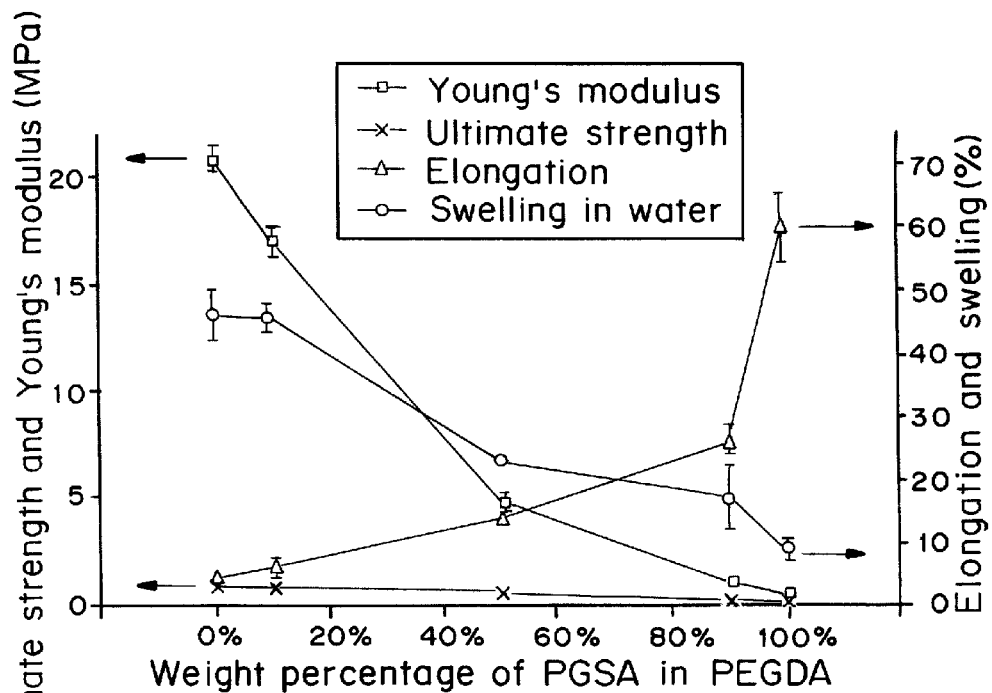
FIG. 12 presents data on Young's modulus, ultimate strength, elongation % and swelling % for various weight percentages of PGSA in PEGD, for copolymerization of PGSA (DA=0.34) and PEG diacrylate (Mw=700 Da) where PEG chains become incorporated as crosslinks between PGSA.

In various embodiments, a liquid acrylated pre-polymer matrix is combined with acrylated hydrogel precursors to impart mechanical, biodegradable, and swelling properties that are not normally associated with typical hydrogel materials (see, FIG. 12). For example, a hydrogel formed from 20% (w/w) poly(ethylene glycol)di-acrylate (PEGD, 700 Da) in water exhibits an elongation of 14%, Young's modulus of 0.54 MPa and ultimate strength of 0.063 MPa. Through combining PEG with PGSA (DA=0.5), the Young's modulus, ultimate strength, elongation and swelling ratio can be precisely controlled (see, FIG. 12). With increasing acrylated pre-polymer concentration the elongation ranged from 4 to 60%, Young's modulus from 20 to 0.6 MPa and ultimate strength from 0.890 to 0.270 MPa (see, FIG. 12). The networks formed by the copolymerization of PEGD with acrylated pre-polymer (DA=0.5) (50:50) showed a ten fold higher Young's modulus and ultimate strength than the typical PEGDA hydrogel while maintaining its elongation at break (see, FIG. 12). Increased elongation was found in materials containing greater then 50% PEGDA. Also, the swelling behavior of these networks can be tuned from 40% to 10% through changing the concentration of acrylated pre-polymer between 10% and 90%. PGSA elastomeric networks are degradable at physiologic conditions and show cell-adhesive and non-cytotoxic properties. As can be seen, the present invention in various embodiments can provide materials and compositions where the degradation rate can be increased without necessarily decreasing the mechanical strength because, it is believed with out being held to theory, of the incorporation of two or more types of cross-links. As it can also be seen, the present invention in various embodiments can provide a degradation rate that is substantially independent of overall crosslink density and/or substantially independent of overall crosslink density within a range of overall crosslink densities.

In various embodiments, a biodegradable material formed from the a composition of the present invention containing a co-polymer, is provided that has one or more of the following properties: (a) a tensile Young's modulus less than about 17 MPa when measured according to ASTM standard D412-98a; (b) a tensile Young's modulus greater than about 0.5 MPa when measured according to ASTM standard D412-98a; (c) a tensile Young's modulus greater than about 0.6 MPa and an elongation of greater than about 20%, both when measured according to ASTM standard D412-98a; (d) a tensile Young's modulus greater than about 0.25 MPa when measured according to ASTM standard D412-98a and a swelling in water of greater than about 1%; (e) a tensile Young's modulus greater than about 0.25 MPa when measured according to ASTM standard D412-98a and a swelling in water of greater than about 20%; (f) a tensile Young's modulus greater than about 0.25 MPa when measured according to ASTM standard D412-98a and a swelling in water of greater than about 40%; (g) a tensile Young's modulus greater than about 0.25 MPa when measured according to ASTM standard D412-98a and a swelling in water of greater than about 80%; (h) a Young's modulus in the range between about 0.4 MPa and about 0.55 MPa when measured according to ASTM standard D412-98a; (i) a maximum elongation greater than about 60%; (j) a maximum elongation greater than about 100%; (k) a maximum elongation greater than about 160%; (l) a degree of acrylation in the range between about 0.25 to about 0.35 and a Young's modulus in the range between about 0.6 and 1.0 MPa when measured according to ASTM standard D412-98a; (m) a degree of acrylation in the range between about 0.25 to about 0.5 and an elongation greater than about 40%; (n) a degree of acrylation in the range between about 0.25 to about 0.35 and a Young's modulus in the range between about 0.6 and 1.0 MPa when measured according to ASTM standard D412-98a, and a crosslink density in the range between about 90 and 120.

Forms and Fabrication of Various Morphologies

The liquid acrylated pre-polymers, and acrylated pre-polymer/co-polymer compositions of the present invention be processed into a wide range of formats and geometries. Referring to FIGS. 7A-D, the acrylated pre-polymer can used to manufacture nanoparticles and/or microparticles of the compositions and materials of the present inventions (FIG. 7A), which was previously not possible with, e.g., PGS due to the processing conditions (thermal curing). In various embodiments, such particles can be used for the controlled release of drugs, e.g., in joints or other mechanically dynamic environments. The acrylated pre-polymer can used to manufacture very thin walled tubes of the compositions and materials of the present inventions (FIG. 7B); the tube illustrated having an inner diameter of about 1 mm and an about 0.20 mm wall thickness. In various embodiments, such tubes cab be used e.g., as small-diameter vascular grafts were made. The acrylated pre-polymer can processed to provide compositions and materials of the present inventions having micropatterned surfaces (FIG. 7C), and porous scaffolds (FIG. 7D). The acrylated pre-polymer can also be processed into thicker (>6 mm) geometries. For example, 20 mm thick geometries were fabricated, which was previously not possible with thermally cured PGS, due to bubble formation. In various embodiments, the ability to form materials and compositions of the present invention into thicker structures without substantial bubble formation, facilitates the formation of complex structures.

The structures illustrated in FIGS. 7A-D, were prepared substantially as follows, acrylated pre polymer with 0.1% phot initiator were molded into various shapes. For scaffolds, the macromer solution was poured overtop a porogen (e.g. sugar, salt) followed by UV polymerization and porogen leaching in water. For micropatterned PGSA, a thin layer of acrylated pre-polymer was replica molded on micropatterned silicon masters and photopolymerized. For tube formation, the acrylated pre-polymer solution was poured into a glass mold and photocured. Nano/micro particles were prepared from the acrylated pre-polymer using an oil-in-water emulsion solvent evaporation procedure (single emulsion method).

Methods of Fabrication

In various aspects the present inventions provide methods of forming biodegradable elastomeric compositions, materials and devices. In various embodiments, to fabricate photocurable biodegradable elastomers at room temperature, the following process can be employed. (1) a pre-polymer, e.g., from glycerol and sebacic acid, is created; (2) functional hydroxyl groups on backbone of the pre-polymer are acrylated and the reaction product subsequently purified; and (3) the acrylated pre-polymer was is photopolymerized with UV light in the presence of a photoinitiator. Where glycerol and sebacic acid is used to form the pre-polymer, the resultant elastomer is referred to as poly(glycerol sebacate adipate) PGSA. In various embodiments, a PGS pre-polymer had a weight average molecular weight (Mw) of 23 kDa and a molar composition of approximately 1:1 glycerol:sebacic acid. To functionalize the pre-polymer with vinyl groups, it can be reacted with different molar ratios of acryloyl chloride, at room temperature.

In various embodiments, where glycerol and sebacic acid is used to form the pre-polymer and acrylation is by acryloyl chloride, the degree of acrylation (DA) increases substantially linearly when the molar ratio of acryloyl chloride to glycerol-sebacate can be varied from 0.3 to 0.8 (see, e.g., FIG. 10) and increasing the DA in PGSA from 0.3-0.8, the can increase the crosslink density, for example, from about 6 to about 185 mol/m$^3$ and the relative molecular mass between crosslinks can be decreased.

In various aspects, to fabricate biodegradable elastomers at room temperature, provided are methods using one or more of a Mitsunobu-type reaction, polymerization using a thermal initiator, redox-pair initiated polymerization, Michael-type addition reaction using a bifunctional sulfhydryl compound, to cross-link the pre-polymers.

Figure 6A:
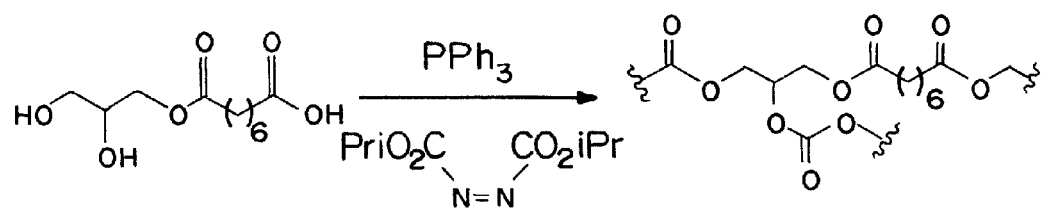
FIG. 6A-C schematically illustrates a formation scheme for an elastomeric composition or material according to various embodiments of the present inventions.

In various embodiments, a Mitsunobu type reaction is used to cross-link the pre-polymer. For example, referring to FIG. 6A, a PGS pre polymer dissolved in THF is reacted, at room temperature and pressure conditions, with diisopropyl azodicarboxylate and triphenylphosphine. Within about 1 hour of reaction time the final elastomeric cross-linked polyester composition product was formed. The mild conditions of this reaction, for example, also permit the incorporation of a variety of functional groups, such as, e.g., esters, epoxides, halides into the elastomeric cross-linked polyester composition.

Figure 6B:
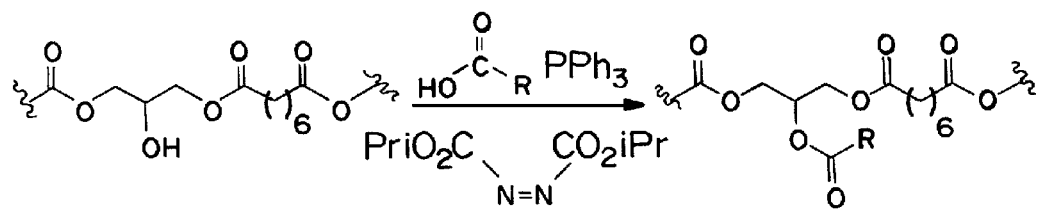
Figure 6C:
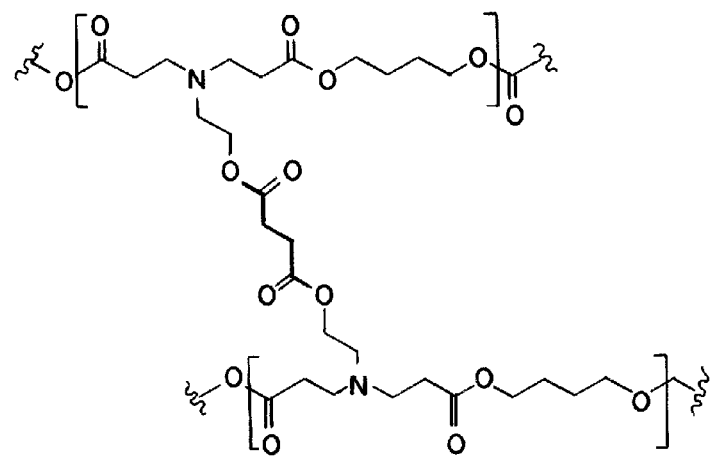

In various embodiments, mono-acids can be used to introduce ester linked side-chains, and mono-alcohols can be used to create ether linked side-chains (see FIG. 6B). In various embodiments, poly-beta amino esters, can be created, a class of biomaterials that have shown promise in gene delivery. One potential limitation in the development of poly-beta amino esters for clinical applications is the inability to synthesize high molecular weight products. The application of the Misunobu-type reaction of the present inventions could be useful in overcoming this obstacle to produce high molecular weight formulations by crosslinking side chains (see, e.g., FIG. 6C). In various embodiments, the present inventions thus include, particles for gene delivery comprising poly-beta amino ester microspheres.

Further Uses and Applications

Due to its elastomeric nature, the compositions and materials of the present inventions can find application in a wide variety of applications including tissue engineering of tissues, especially muscle tissue, artery, and heart valves.

For example, in various embodiments, a biodegradable elastomeric compositions and materials of the present can be used in the form of tubes, e.g., for peripheral nerve reconstruction. Preferably, the tube is constructed to withstand pressure of the surrounding tissue and guide the nerve in its outgrowth, substantially unhampered by scar tissue formation. In peripheral nerve regeneration applications, it is preferred that the material be functionalized (e.g., with GRGD) to facilitate the attachment and guidance of Schwann cells.

For example, in various embodiments, biodegradable elastomeric compositions and materials of the present can be used as a matrix, scaffold, or structure for cell attachment and/or encapsulation. In various embodiments, short-peptides (e.g., GRGD) can be incorporated into the photocured polymer to enhance cell adhesion. Incorporation of these short peptides into the photocured polymer can be achieved by mixing the functionalized peptides with the PGSA followed by photocuring. For example, in various embodiments, a GRGD peptide can be functionalized with a poly(ethylene glycol) spacers and an acrylate group. In various embodiments, the surface of the material can be nano-patterned, e.g., on the inside of the tube, to guide cells. For example, in the case of a nerve graft, the material can be nano-patterned to enhance the cell guidance over the nerve graft and guide the Schwann cells.

In various embodiments, the present inventions provide biodegradable elastomeric compositions and materials as a 3D matrix for the encapsulation and proliferation of cells. In various embodiments, these matrixes are configured for stem cells.

For example, in various embodiments a liquid porogen/cell delivery vehicle consisting of glycerol is formed as a temporary substrate to protect the encapsulated stem cells and to create pores within the resultant PGSA network. PGSA was mixed with glycerol followed by UV curing and submersion into water creating a porous scaffold, which swells in an aqueous solution up to 300%. Human embryonic stem cells dispersed in glycerol, mixed with PGSA, UV cured and placed in cell culture media created an environment for the encapsulated cells to attach and proliferate. Specifically, within 24 hours the stem cells were observed to have attached to the PGSA network, glycerol diffused out of the scaffold and cell culture media diffused into the scaffold. Cell proliferation was observed up to 7 days. The porous scaffolds showed a minimal degradation in vitro and maintained its 3D structure up to 30 days.

The hydroxyl groups on the compositions and materials of the present inventions provide sites to which molecules may be attached to modify the bulk or surface properties of the material. For example, in various embodiments, tert-butyl, benzyl, or other hydrophobic groups can be added to the material to reduce the degradation rate. In various embodiments, polar organic groups such as methoxy can be used to facilitate adjustment of degradation rate and hydrophilicity. In various embodiments, addition of hydrophilic groups, for example, sugars, at these sites can be used to increase the degradation rate.

In various embodiments, acids can be added to the polymer to modify the properties of the material. For example, molecules with carboxylic or phosphoric acid groups or acidic sugars can be added. In various embodiments, charged groups such as sulfates and amines can be attached to the polymer. Groups that are added to the polymer can be added, for example, via linkage to a hydroxyl group (substituting for hydrogen), linked directly to the polymer backbone by substituting for a hydroxyl group, incorporated into an organic group which is linked to the polymer, and/or incorporated into a cross-link as part of the link or as a substituent on the link.

In various embodiments, attachment of such non protein organic or inorganic groups to the polymer can be used to modify the hydrophilicity and the degradation rate and mechanism of the polymer. In various embodiments, protecting group chemistry can be used to modify the hydrophilicity of the material.

In various embodiments, to, for example, facilitate controlling and/or regulating polymer interaction with cells; biomolecules and/or bioactive agents may be coupled to the hydroxyl groups or integrated into the polymer backbone. In various embodiments, biomolecules and/or bioactive agents are encapsulated within the compositions and materials of the present inventions. In various embodiments, the biomolecules and/or bioactive agents are attached to the polymer, e.g., covalently, non-covalently, etc., and attachment can result in a slower release rate.

In various embodiments of compositions and materials of the present inventions including one or more biomolecules and/or bioactive agents, the cross-link density of one or more types of cross links is adjusted by adjusting the degree for acrylation, the proportion of one or more co-polymers, or both, to provide an elastomeric composition or material that has a desired biomolecule and/or bioactive agent release rate, release profile, or both.

In various embodiments, for example, biomolecules such as growth factors can be incorporated into a wound dressing/sealent comprising a composition or material of the present inventions to recruit cells to a wound site and/or promote specific metabolic and/or proliferative behavior in cells that are at the site and/or seeded within the matrix. Exemplary growth factors include, without limitation, TGF-β, acidic fibroblast growth factor, basic fibroblast growth factor, epidermal growth factor, IGF-I and II, vascular endothelial-derived growth factor, bone morphogenetic proteins, platelet-derived growth factor, heparin-binding growth factor, hematopoetic growth factor, and peptide growth factor. In various embodiments, integrins and cell adhesion sequences (e.g., the RGD sequence) can be attached to the compositions and materials of the present inventions to facilitate cell adhesion. In various embodiments, extracellular matrix components, e.g., collagen, fibronectin, laminin, elastin, etc., can be combined with composition, and materials of the present inventions to manipulate cell recruitment, migration, and metabolism and the degradation and mechanical properties of the material. In various embodiments, proteoglycans and glycosaminoglycans can be covalently or non-covalently attached to compositions and materials of the present inventions.

Tissue Engineering Applications

The elasticity and ability to "tailor" the chemical and physical properties of the compositions and materials of the present inventions recommends various embodiments for use in regenerating a variety of tissues. In various embodiments, for example, the compositions and materials of the present inventions can be used to tissue engineer, epithelial, connective, nerve, muscle, organ, and other tissues, as well as artery, ligament, skin, tendon, kidney, nerve, liver, pancreas, bladder, and other tissues. In various embodiments, compositions and materials of the present inventions can be used as the template for mineralization and formation of bone.

Tissues typically experience mechanical forces and deformation in daily use, and tissue remodeling is often influenced by mechanical forces. For example, heart and other muscle will increase in density and size when they are frequently used and will atrophy under disuse. Mechanical force stimulates the cells that produce extracellular matrix elements to produce growth factors that promote either the production or degradation of ECM. Use of a substance, like various embodiments of the compositions and materials of the present inventions, that mimics a normal physiological response to mechanical forces can facilitate the regeneration of normal tissue, as mechanical stimulation can be applied early in the culturing of tissue engineered constructs.

For example, various embodiments of compositions and materials of the present inventions can be used to tissue engineer or regenerate a portion of a patient's bladder. In various embodiments, smooth muscle cells and urothelial cells are seeded onto compositions and materials of the present inventions. The cells can be allowed to proliferate before the implant is placed into a patient. To replace or regenerate cartilage, chondrocytes can be seeded onto various embodiments of the compositions and materials of the present inventions, which can withstand the cyclic shear and compressive forces cartilage is subjected to as joints bend.

In various embodiments, compositions and materials of the present inventions may also be used to produce prosthetic heart valves. Heart valves are very flexible and are subjected to cyclic deformation as the heart beats. The body repairs tears in heart valve through normal physiologic mechanisms and thus can regenerate heart valves made of biodegradable materials. In various embodiments, the present inventions provide a compositions and materials of the present inventions formed in the shape of a heart valve and seeded with smooth muscle cells and endothelial cells to facilitate remodeling in the body to produce a new, non-synthetic heart valve. In various embodiments, it may be desirable to add fibroblasts. In preferred embodiments, the regeneration occurs over a period of 3 months, where the degradation rate of the polymer is controlled by modifying the cross-link density, by modifying the proportion of co-polymer, or both.

The shape of the compositions and materials of the present inventions can be manipulated for specific tissue engineering applications as well as other applications. Exemplary shapes include particles, tubes, spheres, strands, coiled strands, films, sheets, fibers, meshes, and others. In various embodiments, microfabrication can be used to form capillary networks from compositions and materials of the present inventions. For example, a silicon wafer is processed using standard microfabrication techniques to produce a capillary network having a desired pattern. The network is coated with a sacrificial layer, for example, sucrose. The acrylated prepolymer mixture (which can comprise a co-polymer) is cast over the sacrificial layer and cured according to a method described herein. Water can be used to dissolve the sacrificial layer and release the polymerized compositions and materials of the present inventions, which will have a relief pattern of the capillary networks that had been formed in the silicon wafer. In various embodiments, the channels in the compositions and materials of the present inventions are about 7 μm across and about 5 μm deep. It is to be understood, that while the size limit for the channels is dictated by the resolution of the microfabrication technique, biological applications may benefit from channel sizes on the order of 5 to 10's or 100's of microns or larger. The capillary networks can be closed by covering them with a flat sheet of compositions and materials of the present inventions and curing it. For example, a layer of uncrosslinked polymer can be used as a glue between the patterned layer and the flat layer. Polymerizing the "glue" can knit the two pieces together. Further curing of the assembly can increase the cross-link density of the glue and form covalent bonds between the glue and the flat and patterned compositions and materials of the present inventions layers. In various embodiments, an uncrosslinked flat compositions and materials of the present inventions film can be cured over a patterned film to cover the channels.

These shapes can be exploited to engineer a wide variety of tissues. For example, the polymer can be fabricated into a tube to facilitate nerve regeneration. The damaged nerve is fed into the end of the tube, which guides the migration of axons across the wound site. In various embodiments, compositions and materials of the present inventions can be used to fabricate the tissue structures of liver. For example, formed into a network of tubes that mimic a blood vessel and capillary network which can be connected to a nutrient supply to carry nutrients to the developing tissue. Cells can be recruited to the network of tubes in vivo, and/or it can be seeded with blood vessel cells. Around this network of tubes, compositions and materials of the present inventions can be formed into networks imitating the arrangements of extracellular matrix in liver tissue and seeded with hepatocytes. Similarly, various embodiments of the compositions and materials of the present inventions can be fabricated into a fibrous network, seeded with islet cells, and used to tissue engineer pancreas. The compositions and materials of the present inventions can also be seeded with a variety of other cells, for example, tenocytes, fibroblasts, ligament cells, endothelial cells, epithelial cells, muscle cells, nerve cells, kidney cells, bladder cells, intestinal cells, chondrocytes, bone-forming cells, stem cells such as human embryonic stem cells or mesenchymal stem cells, and others.

Medical Applications

Other medical applications may also benefit from the elasticity of the polymer of the invention. For example, after abdominal surgery, the intestines and other abdominal organs tend to adhere to one another and to the abdominal wall. It is thought that this adhesion results from post-surgical inflammation, however, anti-inflammatory drugs delivered directly to the abdominal region dissipate quickly. In various embodiments, compositions and materials of the present inventions can be used to deliver anti-inflammatory drugs to the abdominal region. Because the compositions and materials of the present inventions can be provided in embodiments that are soft and flexible, yet biodegradable, they can be implanted between the abdominal wall and internal organs, for example, by attaching it to the abdominal wall, without cutting internal organs, which would lead to infection. The anti-inflammatory drug can be released from the compositions and materials of the present inventions over a period of time, e.g., months. While previous researchers have attempted to use hydrogels, hyaluronic acid-based membranes, and other materials to solve these problems, such materials tend to degrade quickly in the body; a longer resident period is necessary to prevent adhesion.

In various embodiments, compositions and materials of the present inventions can be used to coat a metallic stent. Because compositions and materials of the present inventions can be provided in embodiments that are flexible, it will expand with the stent without ripping, while the stiffness of the metal stent will prevent the compositions and materials of the present inventions from elastically assuming its previous shape. The compositions and materials of the present inventions can be include one or more anti-coagulant and/or anti-inflammatory agents to facilitate preventing, e.g., the formation of clots or scar tissue. Angiogenic agents can be included to promote the remodeling of the blood vessel surrounding the stent.

In various embodiments, compositions and materials of the present inventions can also be used to prepare "long term" medical devices. Unlike typical permanent medical devices, compositions and materials of the present inventions can be made to degrade over time, for example, they can be fabricated into a biodegradable cardiac stent. Preferably, compositions and materials of the present inventions are combined with a harder polymer that plastically forms for the production of stents. In various embodiments, the compositions and materials of the present inventions acts as a plasticizer that enables the stent to expand into the desired shape after implantation. The stent increases the diameter of the blood vessel to allow easier circulation, but, because the stent is biodegradable, surrounding blood vessels increase in diameter without thrombosis or covering the stent with scar tissue, which could reclose the blood vessel. The time the stent should remain in place and retain its shape before degradation will vary from patient to patient and depend partially on the amount of blockage and the age of the patient (e.g., older patients require more time to heal). Using the teachings presented herein, one of ordinary skill in the art can adjust one or more of, e.g., the DA, the cross-link density, and the co-polymer proportion in those embodiments having a co-polymer, to adjust the degradation rate. As for the coated stent, a degradable stent of the present invention can also release biomolecules, bioactive agents, or some combination of these in situ.

In various embodiments, the compositions of the present inventions can be used as surgical glue. A biocompatible, biodegradable surgical glue could be used to stop bleeding during surgery but does not need to be removed before the surgeon sutures the wound closed and will degrade over time. Current surgical glues often use fibrin derived from bovine tissue, and a synthetic surgical glue reduces the risk of Creuzfeld-Jakob syndrome ("mad cow disease"). To produce a glue, it is preferred to increasing the number of hydroxyl groups (e.g., by reducing the cross-link density), and rendering the product exceedingly sticky. In various embodiments, a surgical glue of the present invention has a cross-link density less than 1%, preferably less than 0.5%, and more preferably less than 0.05%.

In various embodiments, compositions and materials of the present inventions can be used to support in vivo sensors and catheters. The polymer can be constructed into a chamber for an optical fiber-based sensor or a coating for a catheter that is inserted into the area of interest. In a sensor, the chamber can contain a specific chromophore-bonded receptor for the molecule of interest. When an analyte attaches to the receptor, the chromophore will either emit or absorb light at an specific wavelength. The absorption or emission may be detected by an apparatus connected to the optical fiber. The sensor may be used for, for example, short term, continuous monitoring, for ten to fifteen days. Likewise, a catheter may be used to periodically deliver drugs or other small molecules or bioactive agents to a specific site or intravenously. Use of various embodiments of the compositions and materials of the present inventions can reduce the formation of scar tissue which would ordinarily form around a shunt or other implant that is used for more than two weeks. It is preferred, in various embodiments, that the degradation rate of the compositions and materials of the present inventions are chosen so that there is no significant degradation of the material while it is in place in the patient.

Drug Release Applications

In various embodiments, compositions and materials of the present inventions can be used for drug release applications, for example, in applications where the matrix retaining the drug needs to be flexible. Because compositions and materials of the present inventions can provide embodiments that are elastic, they can move with the patient as he/she walks, runs, sits, etc. Because compositions and materials of the present inventions can provide embodiments that maintain their mechanical integrity as they degrades, the device is less likely to fail catastrophically toward the end of its lifetime, reducing the risk of a bolus release of the desired agent. Biomolecules and bioactive agents can all be combined with various embodiments of the compositions and materials of the present inventions using covalent or non-covalent interactions. Exemplary non-covalent interactions include hydrogen bonds, electrostatic interactions, hydrophobic interactions, and van der Waals interactions.

In various embodiments, compositions and materials of the present inventions may also be used for other wounds that are hard to close or that fail to heal properly through normal physiologic mechanisms. For example, diabetics often get skin injuries ("diabetic ulcers"), especially in the lower extremities, that take a long time to heal or fail to heal properly due to poor circulation. The use of various embodiments of the compositions and materials of the present inventions to deliver antibiotics or anti-inflammatory agents to these wounds can aid healing and provide a cover for the wound.

Non-Medical Applications

In various embodiments, compositions and materials of the present inventions can be used for non-medical applications. For example, diapers are formed from a tough elastomer and liquid-permeable topsheet that encase an absorbent material. Currently, polypropylene is used for the elastomeric "casing". Polypropylene is not degradable and requires ten or more years to break down in a landfill. In contrast, compositions and materials of the present inventions can provide embodiments that are stable in a dry environment but will degrade in a landfill within two to four weeks after becoming wet. Similar products that can exploit the biodegradability of compositions and materials of the present inventions include incontinence protectors, sanitary napkins, panty liners, and wound dressings. Likewise, plastic bags, e.g., trash bags, can be made partially or entirety of various embodiments of the polymers of the present inventions. Where compositions and materials of the present inventions are used alone, it may be desirable to increase the cross-link density, and/or increase the proportion of co-polymer, and/or modify the hydroxyl groups to increase the degradation time and prevent significant degradation before the bag reaches the landfill.

In various embodiments, compositions and materials of the present inventions can be exploited to protect not only natural resources but the animals that depend on those natural resources. For example, it is very popular to release helium filled balloons at various public events. The balloons eventually pop and drift back down to earth, where animals may choke while attempting to eat them. In contrast, balloons made out of various embodiments of the compositions and materials of the present inventions would degrade upon exposure to the elements. Such balloons could eventually be digested by animals that eat them and would not present a continuing choking risk to animals once they degraded. In various embodiments, compositions and materials of the present inventions may be used to fabricate fishing lures or flies. When a fisherman loses a lure, the lure will simply sink to the bottom of the stream or lake and eventually degrade.

In another non-medical application, various embodiments of the compositions and materials of the present inventions can be used as a base for chewing gum. For example, the material may be combined with a colorant, flavor enhancer, or other additive to produce a gum. The appropriate microstructure to produce a pleasant mouthfeel during chewing can be determined by polymerizing the polymer to different molecular weights and cross-link densities and chewing the resulting material for a few minutes.

The gum can also be adapted to deliver nutrients (e.g., vitamins) or drugs to the chewer. Nutrients may include FDA-recommended nutrients such as vitamins and minerals, amino acids, or various nutritional supplements available at health food stores. Such additives may simply be mixed with the acrylated pre-polymer (with or without a co-polymer) to produce a gum. In various embodiments, the nutrients can be covalently attached to the polymer, preferably through hydrolyzable bonds or bonds that are lysed by the enzymes found in the mouth. As the gum is chewed, the nutrient or drug is released and swallowed.

EXAMPLES

Aspects of the present inventions may be further understood in light of the following examples, which are not exhaustive and which should not be construed as limiting the scope of the present inventions in any way.

The following examples provide examples of the preparation of PGSA networks and compare the properties of: (a) thermally cured poly(glycerol sebacate) (PGS); (b) photocured poly(glycerol sebacate)-acrylate (PGSA); and (c) and photocured poly(glycerol sebacate)-acrylate-co-poly(ethylene glycol) (PGSA-PEG) networks. In the Examples, these polymers were examined for their degradation characteristics in vitro and in vivo), mechanical properties and biocompatibility in vivo.

Example 1

PGS, PGSA and PGSA-PEG Copolymers

Synthesis of the Pre-Polymer and Acrylated Pre-Polymer

All chemical were purchased from Sigma-Aldrich (Milwaukee, Wis., USA), unless stated otherwise, pre-polymer was synthesized by polycondensation of equimolar glycerol and sebacic acid (Fluka, Buchs, Switzerland) at 120° C. under argon for 24 h before reducing the pressure from 1 torr to 40 mtorr over 5 h, resulting in a viscous liquid. The acrylation of the pre-polymer was prepared from the pre-polymer without further purification. The polycondensation was continued for another 24 h, yielding a viscous pre-polymer. This material was used without further purification.

A flame-dried round-bottom flask was charged with PGS pre-polymer (20 g, with 78 mmol hydroxyl groups), 200 mL anhydrous dichloromethane, to make a 10% solution (w/v). After adding 20 mg 0.18 mmol) of the catalyst 4-(dimethylamino)-pyridine (DMAP), the reaction flask was cooled to 0° C. under a positive pressure of nitrogen and stirred. Once cooled, 0.1 to 1.1 (mol/mol) acryloyl chloride (0.25-0.80 mol per mol hydroxyl groups on PGS pre-polymer) to glycerol-sebacate was slowly added to start the reaction, and an equimolar amount of triethylamine to acryloyl chloride was added in parallel. The mixture was allowed to heat up to room temperature and stirred for an additional 24 h under nitrogen. The product was dissolved in ethyl acetate to precipitate the chloride salts, filtered and dried at 45° C. and 5 Pa providing a viscous liquid.

Characterization of the Pre-Polymer and Acrylated Pre-Polymer

Pre-polymer and acrylated pre-polymer samples were dissolved in $CCl_3D$ and $^1H$ Nuclear Magnetic Resonance ($^1H$-NMR) spectra were recorded on a Varian Unity-300 NMR spectrometer. Chemical shift in ppm for NMR spectra were referenced relative to $CCl_3D$ at 7.27 ppm. Composition was determined by calculating the signal intensities of —$COCH_2CH_2$—$CH_2$— at 1.2, 1.5, 2.2 ppm for the sebacic acid, —$CH_2$=$CH$— at 3.7, 4.2 and 5.2 ppm for glycerol and —$CH$=$CH_2$ at 5.9 ppm, 6.1 ppm and 6.5 ppm for the protons on the methylene groups. The signal intensity of the methylene groups of the sebacic acid (1.2 ppm) and the acrylate groups (average signal intensity of 5.9, 6.1 and 6.5 ppm) were used to calculate the degree of acrylation (DA).

Figure 8A:
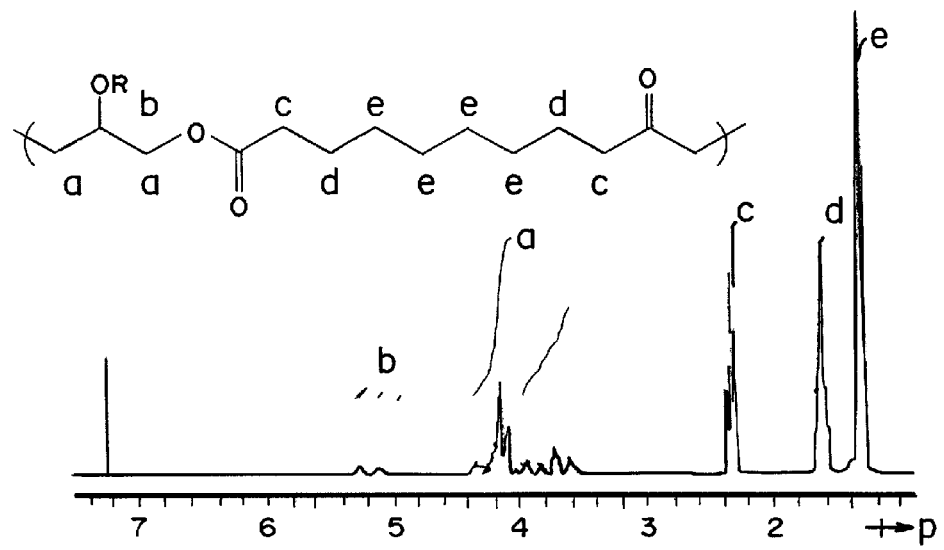
FIGS. 8A and 8B show $^1$H-NMR spectra.
Figure 8B:
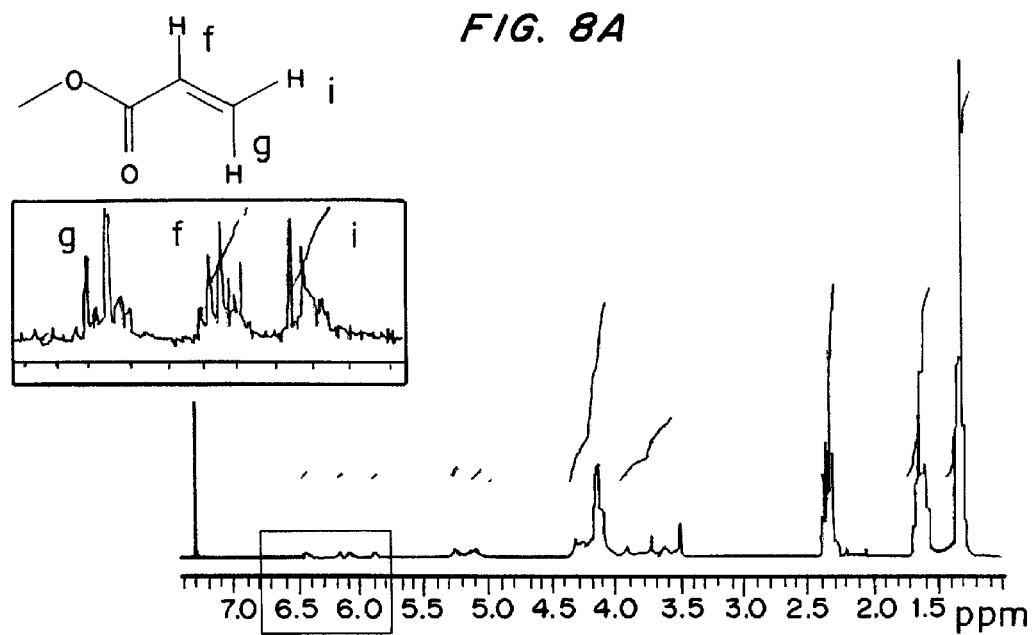

The PGS pre-polymer had a weight average molecular weight (Mw) of 23 kDa and a molar composition of approximately 1:1 glycerol:sebacic acid, as confirmed by GPC and $^1H$-NMR analyses. Example spectra are shown in FIGS. 8A and 8B. FIG. 8A showing a spectrum of PGS pre-polymer and FIG. 8B of PGSA. Referring to FIGS. 8A and 8B, the sebacic acid and glycerol in the polymer matrix were identified at 1.2, 1.5, 2.2 ppm and 3.7, 4.2 and 5.2 ppm by hydrogens located on the carbons labeled 'a'-'e' in the figures. Vinyl groups located on the PGSA were identified at 5.9 ppm, 6.1 ppm and 6.4 ppm labeled 'f'-'i' in the figures, where the region about g, f and I has been expanded in the inset 8X02.

FIGS. 9A and 9B compare ATR-FTIR spectra of: PGS pre-polymer PGS pre-polymer (902); PGSA with a DA of 0.20 (904); PGSA (DA=0.54) (906); thermally cured PGS (908); photocured PGSA (DA=0.20) (910); and photocured PGSA (DA=0.54) (912). The formation of a polymer network after photocuring of PGSA is confirmed by the increase of the band at 2930 $cm^{-1}$ corresponding to the vibration of methylene groups and the elimination of the band at 1375 $cm^{-1}$ corresponding to the vibration of the vinyl bonds.

Figure 10:
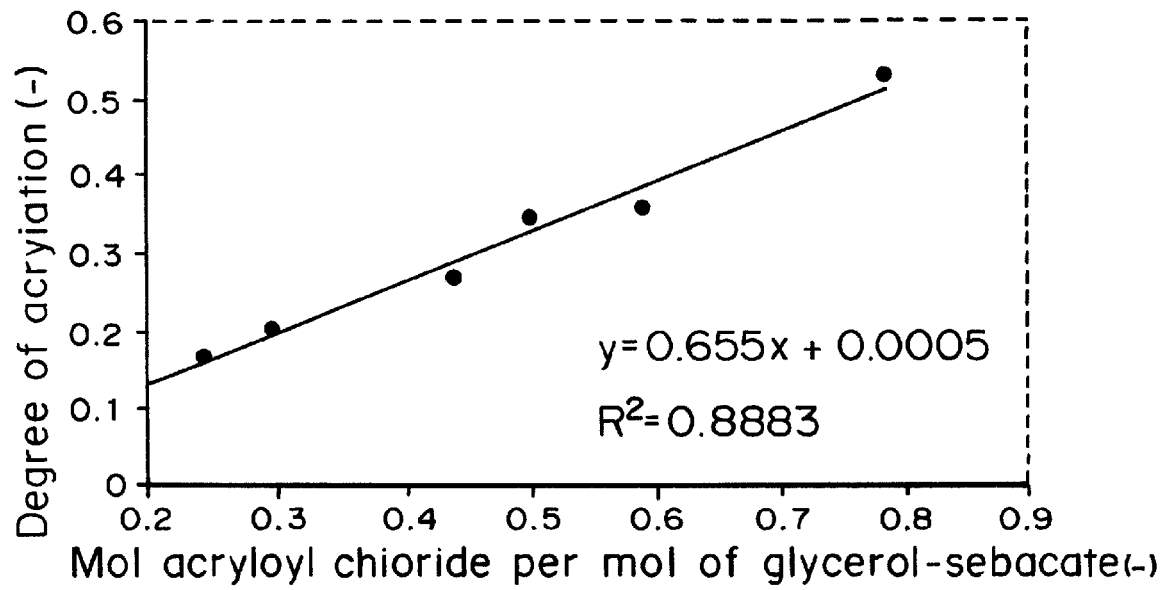
FIG. 10 is a plot of the degree acrylation of the PGSA versus the moles of acryloyl chloride added to the pre-polymer per mole of glycerol-sebacate (–).

The incorporation of acrylate groups was confirmed by the appearance of the peaks at ⏠ 5.9, 6.1 and 6.4 ppm (compare FIGS. 8A and 8B) and by ATR-FTIR by the appearance of the band at 1375 $cm^{-1}$ corresponding to the vibration of the vinyl bond (compare FIGS. 9A and 9B). About 66% of the acryloyl chloride added in the was incorporated in the prepolymer as calculated from signal intensities of $^1H$-NMR, consequently the degree of acrylation ranged from 0.17 to 0.54 as shown in FIG. 10. In addition, the NMR data show that acryloyl chloride apparently reacts preferentially with the hydroxyl groups from glycerol compared with the carboxylate groups from sebacic acid. This was indicated by the increase of signal integral at ⏠ 5.2 ppm corresponding to the resonance of protons from the tri-substituted glycerol and the decrease of signal integral at about ⏠ 3.7 ppm corresponding to the resonance of protons from mono-substituted glycerol (compare FIGS. 8A and 8B) with the increasing of DA. $^1H$-$^1H$ COSY NMR; and quantitative $^{13}C$-NMR analysis showed minimal (<5%) substitution of terminal carboxylate groups (data not shown). The $M_W$ of the PGSA remained substantially unchanged after acrylation.

The PGS pre-polymer and PGSA were sized using gel permeation chromatography (GPC), using THF on Styragel columns (series of HR-4, HR-3, HR-2, and HR-1, Waters Corp., Milford, Mass., USA).

Preparation of Photocured PGSA Networks

PGSA networks were formed by mixing PGSA with 0.1% (w/w) photo initiator (2,2-dimethoxy-2-phenyl-acetophenone) and the polymerization reaction initiated by ultraviolet light at about 4 $mW/cm^2$, between two glass slides with a 1.2 mm spacer, for 10 minutes using a longwave ultraviolet lamp (model 100AP, Blak-Ray). Attenuated total reflectance-Fourier transform infrared spectroscopy (ATR-FTIR) analysis was performed on a Nicolet Magna-IR 500 spectrophotometer to confirm the crosslink reaction. The samples analyzed: (a) thermally cured PGS slabs; (b) photocured PGSA slabs, (e) PGS pre-polymer, and (d) PGSA; were first dissolved in chloroform and then placed on top of the crystal.

Copolymerization of PEG Diacrylate and PGSA

Networks of PGSA-PEG diacrylate were prepared by mixing 10, 50, 90% (wt/wt) PGSA (DA=0.34) with PEG diacrylate (Mw=700 Da) including 0.1% (w/w) photoinitiator, followed by photopolymerization under ultraviolet light between two glass-slides with a 1.2 mm spacer, for 10 minutes. The photocured networks were soaked in 100% ethanol for 24 h and soaked in phosphate buffer saline (PBS) for 24 h prior to mechanical testing. Poly(ethylene glycol) hydrogels were prepared from a PEG diacrylate solution (20%, w/w, in water) containing 0.1% (w/w) photoinitiator, followed by photopolymerization using the conditions described above. The swelling ratio in PBS was determined as described below.

Thermal and Mechanical Properties

The thermal properties of discs from thermally cured PGS, photocured PGSA (DA=0.31, 0.54) and PGSA (DA=0.34+5% PEG diacrylate) were characterized using differential scanning calorimetry (DSC), DSC Q 1000, 2 cycles, within the temperature range of −90° C. and 250° C. using a heating/cooling rate of 10° C. The glass transition temperature (Tg) was determined as the middle of the recorded step change in heat capacity from the second heating run.

Tensile strength tests were conducted on dog-bone-shaped polymer strips (115×25×1.2 mm) cut from photocured PGSA sheets and were tested using an Instron 5542 substantially according to ASTM standard D412-98a. The elongation rate was 50 mm/min and all samples were elongated to failure. Values were converted to stress-strain and the tensile Young's modulus was calculated from the initial slope (0-10%). All the mechanical testing was performed under wet conditions (soaked in PBS for 24 h.) after sol content removal. The sol content, or unreacted macromers, were removed by soaking the PGSA sheets in ethanol for 24 h. To assess the sol content, swelling properties and the dry mass of photocured PGSA, discs (10×2 mm) (n=3) were weighed ($W_0$) and immersed in 5 mL of ethanol. After soaking the samples in ethanol for 24 h the polymer was dried at 90° C. for 7 days and re-weighed ($W_1$) to determine the percentage of unreacted macromers, the sol content ($W_{sol}$), by the following formula $W_{sol}$=[($W_0$−

$W_1)/(W_1)\times100$]. The photocured PGSA discs (without sol content) were soaked in phosphate buffer saline (PBS) for 24 h, surface PBS was removed with a tissue paper and samples were re-weighed (Ws). The swelling ratio (SR) was determined by: SR=[(Ws−$W_0$)/($W_0$)×100] and expressed as a percentage of $W_0$. The swelling ratio of photocured PGSA in ethanol was assessed in the same manner.

To determine the density of the photocured PGSA, a 50 mL pycnometer bottle (Humboldt, MPG. Co.) was used to measure the volume of pre-weighed polymer sample (n=10). The density and Young's modulus of the samples were used to calculate the crosslinking density and relative molecular mass between crosslinks (Mc) substantially as described in, Wang Y, Ameer G A, Sheppard B J, Langer R., *Nat. Biotechnol* 20(6): pp 602-6 (2002), the entire contents of which are incorporated herein by reference.

In Vitro Degradation

To assess full degradation via hydrolysis and relative degradation rates among samples, discs of dry thermally cured PGS, photocured PGSA (DA=0.31, 0.54), and PGSA (DA=0.34+5% PEG diacrylate) polymers (diameter 10'1.6 mm) were weighed (W0) and immersed in 20 mL of 0.1 mM NaOH at 37° C. Prior to the degradation study the sol content was removed, as described above. At 5 different time points (0, 1.5, 3, 4.5, and 6 hours) samples (n=3) were removed from 0.1 mM NaOH and washed with deionized water. Samples were dried at 90° C. for 7 days and weighed (Wt) again. The remaining dry mass [(Wt/W0)'100] was calculated. For surface analysis of the degraded samples by scanning electron microscopy, dry samples were sputter-coated with platinum/palladium (about a 250 Angstrom thick layer), mounted on aluminum stubs with carbon tape and examined on a JEOL JSM-5910 scanning electron microscope.

In Vitro Cell Attachment and Proliferation

Photocured PGSA (DA=0.34) spin coated discs (diameter 18 □1 mm) (n=3), prepared with 20% PGSA in dimethylsulfoxide (DMSO) at 3,400 rpm for 5 min followed by a 10 min UV polymerization, were used in this study. To ensure successful PGSA spin coating and subsequent photocuring, discs with and without UV curing were submerged in Chloroform for 24 h, where unreacted macromers are expected to dissolve. The resultant surfaces were examined using light microscopy. Cell culture medium, Dulbecco's Modified Eagle Medium (DMEM) with 10% fetal bovine serum and 1% Penicillin/Streptomycin, was used as growth medium. The photocured spin coated PGSA discs were incubated with growth medium in a 12 well plate for 4 h in order to remove photo initiator, residual DMSO, and any unreacted monomers prior to human foreskin fibroblast cell (ATCC CRL-2522) seeding. Each disc was seeded with 5,000 cells/$cm_2$ using 2 mL of growth medium. The cells were incubated in, a 5% $Co_2$ humidified incubator at 37° C. After incubation for 4 h the cultures were washed with PBS twice to remove unattached cells and incubated with cell culture medium. Cells were fixed with 4% formaldehyde solution for 10 min and washed with PBS for 4 hours, 2, 5 and 12 days. The cells were then counted at nine random equally sized spots (0.005 $cm^2$) under light microscopy and the cell density was calculated.

Characterization and Comparison of Properties of Cured PGS and PGSA

The UV polymerization of PGSA in the presence of the photoinitiator 2-dimethoxy-2-phenyl-acetophenone yielded elastomeric networks. ATR-FTIR analysis of the photocured PGSA elastomers (FIG. 9A) shows an increase of the band at 2930 $cm^{-1}$ corresponding to the vibration of methylene groups and a decrease of the band at 1375 $cm^{-1}$ corresponding to the vibration of the vinyl bonds. This indicates that most of the vinyl groups participated in the crosslinking reaction. The broad peak at 3475 $cm^{-1}$ was assigned to hydrogen bonded hydroxyl groups. It is believed that these hydrogen bonded hydroxyl groups arise from free hydroxyl groups which are not modified by acryloyl chloride. The Tg of thermally cured PGS, photocured PGSA (DA=0.31, 0.54) and PGSA (DA=0.34+5% PEG Diacrylate) were, respectively, −28.12, −32.2, −31.1 and −31.4° C. These results indicate that thermally cured PGS and photocured PGSA are amorphous at 37° C. Further data on the physical properties of the photocured PGSA is given in Table 1.

TABLE 1

| PGSA, degree of acrylation (DA) | Density (g/cm3) | Young's modulus (Mpa) | Elongation (%) | Ultimate strength (Mpa) | Crosslinking density (mol/m3) | Relative molecular mass between crosslinks (Mc) (g/mol) |
|---|---|---|---|---|---|---|
| 0.17 | 1.21 {0.02} | 0.048 {0.005} | 170 {17.2} | 0.054 {0.005} | 6.4 {0.7} | 18906 {232} |
| 0.20 | 1.19 {0.02} | 0.148 {0.004} | 101 {26.5} | 0.109 {0.011} | 19.8 {0.6} | 6013 {253} |
| 0.31 | 1.16 {0.02} | 0.383 {0.028} | 54.7 {14.1} | 0.163 {0.034} | 51.5 {3.9} | 2262 {185} |
| 0.34 | 1.15 {0.01} | 0.568 {0.222} | 60.1 {5.73} | 0.270 {0.032} | 76.4 {3.0} | 1514 {73.3} |
| 0.41 | 1.15 {0.02} | 0.895 {0.052} | 51.1 {7.41} | 0.364 {0.034} | 120.4 {7.0} | 953.9 {69.1} |
| 0.54 | 1.15 {0.01} | 1.375 {0.084} | 47.4 {11.3} | 0.498 {0.079} | 185.0 {11.3} | 620.1 {42.4} |

Figure 11A:
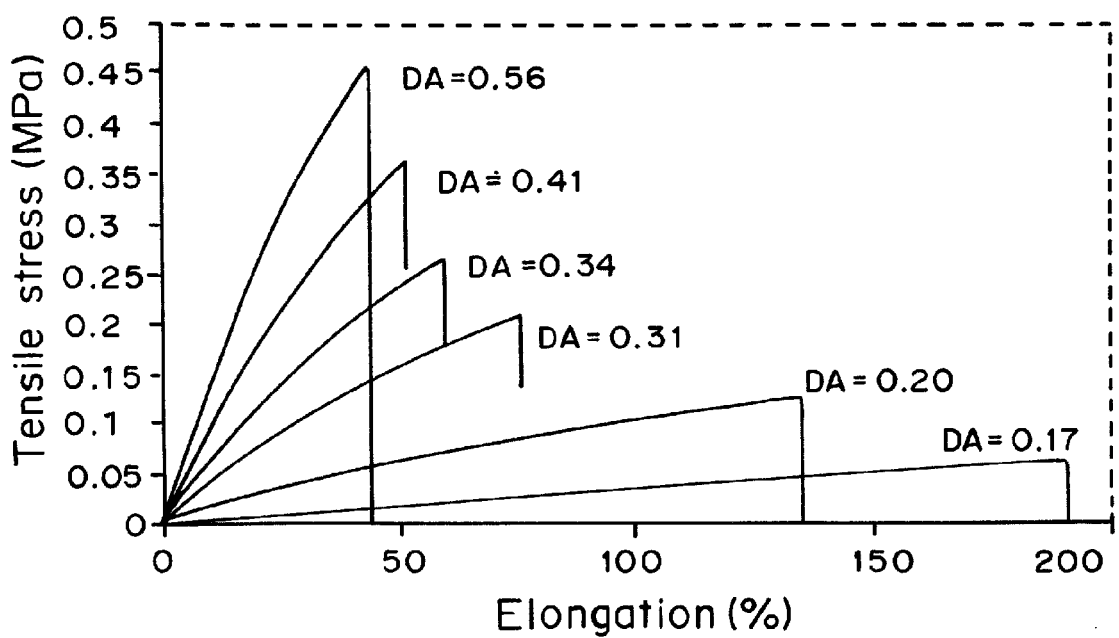
FIGS. 11A-C present data on various properties for various degrees of acrylation (DA) of the photocured PGSA of Example 1; where
Figure 11B:
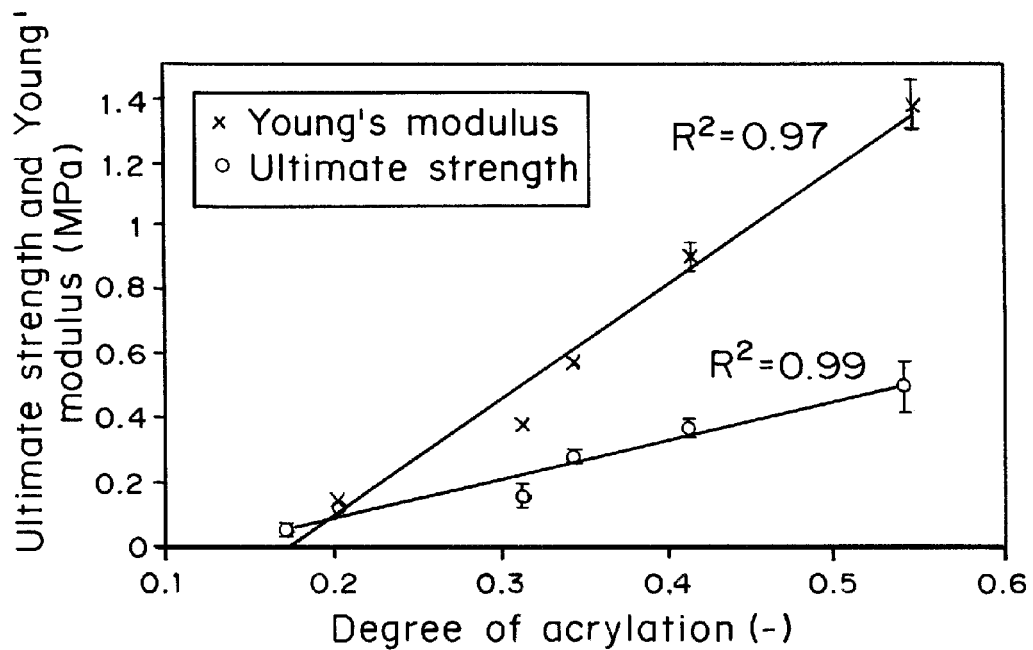

The Young's modulus and ultimate tensile strength of the photocured PGSA was linearly proportional to the DA (data is presented in FIGS. 11A, 11B and Table 1); no permanent deformations were observed after mechanical testing. The mechanical properties of the photocured PGSA spanned from soft to relatively stiff as determined by the tensile Young's modulus of the polymer, which varied from about 0.05 MPa (DA=0.17) to about 1.38 MPa (DA=0.54). The ultimate tensile strength ranged from about 0.06 MPa to about 0.47 MPa (FIG. 3B) whereas the strain to failure of photocured PGSA ranged from about 189% to about 42% with increasing DA. The degree of swelling of the elastomeric networks in ethanol and water ranged, respectively, from about 50 to about 70%, and from about 8 to about 12%. The degree of did not change appreciably as a function of DA. The high degree of swelling in ethanol can facilitate removal of unreacted monomers or potential incorporation of specific factors. The low degree of swelling in water can facilitate, e.g., maintaining the mechanical properties upon implantation.

Figure 11C:
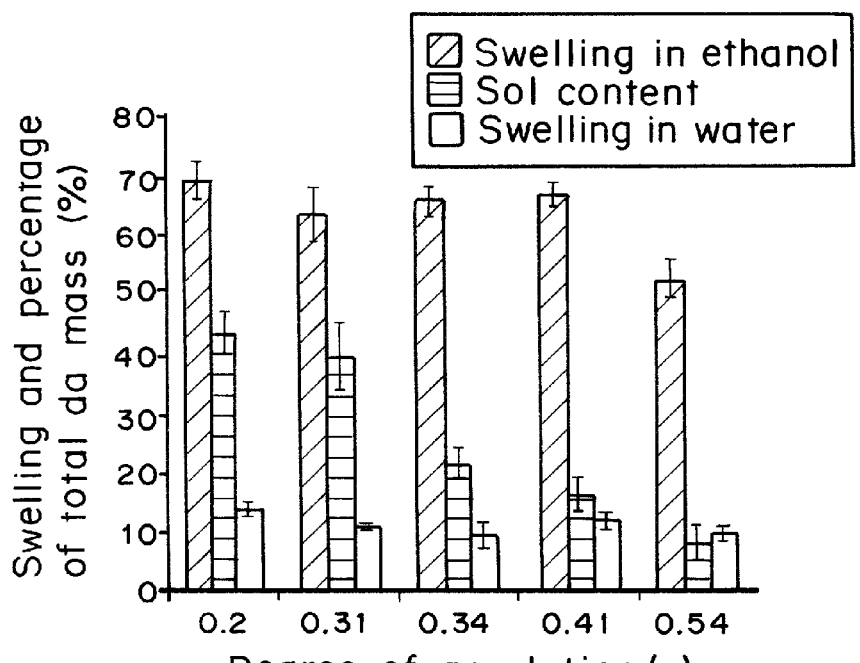

The sol content of the polymer decreased from about 40% to less than about 10% by increasing the DA from about 0.20 to about 0.54 (data is presented in FIG. 11C). It is believed that this is a consequence of the increasing number of new crosslinks between the polymer chains and therefore directly related to the crosslink density. The high sol content that is achieved with a lower DA (softer materials) might be unfavorable, for example, for in situ polymerization where unreacted macromers might diffuse into the surrounding tissue. It was observed that the mechanical properties (measured without sol content) are substantially linearly proportional to the DA, which is correlated to the formation of new crosslinks within the polymer network.

The density of the photocured elastomeric discs was seen to decrease slightly with increasing DA (data is presented in Table 1), which is similar to other thermally cured elastomers in which the density is inversely proportional to the curing time. The density and Young's modulus of the samples was used to calculate the crosslinking density and relative molecular mass between crosslinks (Mc) (data is presented in Table 1). Increasing the DA in photocured PGSA from about 0.17 to about 0.54, increased the crosslinking density from about 6.4 to about 185 mol/m$^3$ and decreased the relative molecular mass between crosslinks from about 18 kDa to about 0.6 kDa.

Copolymerization of PEG Diacrylate and PGSA

In various embodiments, the present inventions provide a photocurable PGSA composition comprising acrylated hydrogel precursors. In various embodiments, the inclusion of an acrylated hydrogel can be used to impart, for example, one or more of mechanical, biodegradable, and swelling properties that, for example, are not normally associated with more common hydrogel materials. FIG. 12 presents some data on the variation of properties of a photocurable PGSA composition comprising various portions of an acrylated hydrogel. Most hydrogel materials are very fragile and have poor mechanical properties. For example, a hydrogel formed from 20% (w/w) poly(ethylene glycol)diacrylate (700 Da) in water exhibits an elongation of 14%, Young's modulus of 0.54 MPa and ultimate strength of 0.063 MPa. Through combining PEG diacrylate with PGSA (DA=0.34), the Young's modulus, ultimate strength, elongation and swelling ratio can be varied (see data presented in FIG. 12). For example, through increasing the concentration of PGSA, the elongation increased from about 4 to about 60%, Young's modulus decreased from about 20 Mpa to about 0.6 MPa and ultimate strength decreased from 0.890 Mpa to about 0.270 MPa. The networks formed by the copolymerization of PEG diacrylate with PGSA (DA=0.34) (50:50) showed a ten fold higher Young's modulus and ultimate strength than the typical PEG diacrylate hydrogel while maintaining elongation. Furthermore, the swelling behavior of these networks was tuned from about 40% to about 10% through changing the concentration of PGSA from about 10% to about 90%.

In Vitro Degradation Results

Figure 13:
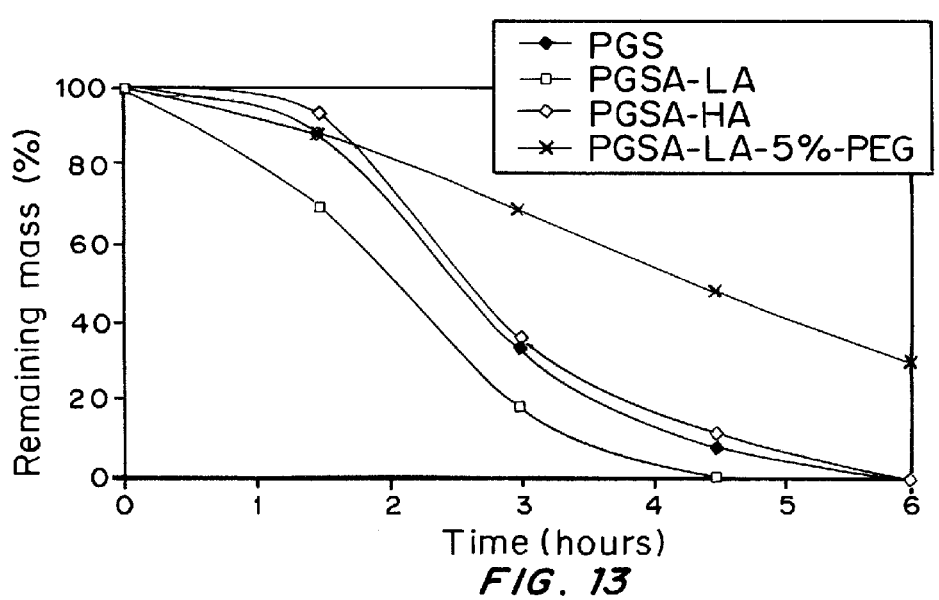
FIG. 13 presents data on the in vitro degradation of PGS (filled diamond symbols), photocured PGSA (DA=0.31, 0.54) (open square symbols for DA=0.31, open diamond symbols for DA=0.54) and PGSA (DA=0.34+5% PEG diacrylate) ("x" symbols) in NaOH (0.1 mM) for 0, 1.5, 3, 4.5, and 6 hours at 37° C. (standard deviation was smaller than 5% of mean).

To examine the relative differences in terms of degradation between the PGS and PGSA polymer networks, a degradation study was performed using high pH to accelerate the hydrolysis. Therefore, photocured PGSA (DA=0.31 and 0.54), PGSA (DA=0.34 copolymerized with 5% PEG diacrylate) and PGS were degraded in a sodium hydroxide (0.1 mM) solution substantially as describe in, Yang J, Webb A R, Pickerill S J, Hageman G, Ameer G A. Biomaterials; 27(9), pp. 1889-98 (2006), the entire contents of which are incorporated herein by reference. Photocured PGSA (DA=031 and 0.54) showed a similar degradation profile as PUS. However, the mass loss of PGSA (DA=0.31) was significantly (P<0.01) higher compared to PGS and PGSA (DA=0.54). The mass loss of PGSA (DA=0.34 copolymerized with 5% PEG diacrylate) was significantly (P<0.01) lower compared to PGS and PGSA (DA=0.54) after 3 hours of degradation in sodium hydroxide. Copolymerization of 5% PEG diacrylate with PGSA (DA=0.34) resulted in polymers with similar mechanical properties (see above and FIG. 12), yet slower degradation rates compared to photocured PGSA (DA=0.54) and PGS, as illustrated in FIG. 13. These results indicate that the in vitro hydrolytic degradation rate of photocured PGSA can be decreased, independent of the starting mechanical strength. SEM analysis of all degraded materials after 3 h in sodium hydroxide show no observable deterioration of gross morphology, or formation of cracks or tears on the surface of the material (SEM data is present in FIG. 14A). Thermal analysis of all degraded materials after 3 h in sodium hydroxide did not show appreciable change in Tg.

In Vitro Cell Attachment

In vitro cell culture shows that various embodiments of the photocured PGSA elastomers of the present inventions support cell adhesion and proliferation. It was observed 59±12% of the human foreskin fibroblasts cells seeded on photocured PGSA attached after 4 h and were viable. The attached cells proliferated, forming a confluent cell monolayer (see FIGS. 14A, 14B and 14C), indicating that in various embodiments a photocured PGSA of the present inventions can function as a cell adhering biomaterial.

Example 2

In Vivo Data and Biocompatability

This example presents data on the modulation of the mechanical properties and the degradation rate of various embodiments of a PGSA composition of the present inventions. Data is presented on the effects of varying the density of acrylate groups in the polymer backbone and data is presented for compositions of PGSA copolymerized with various proportions of low molecular weight poly(ethylene glycol)diacrylate. Data is presented on the influence of these modifications on the biomaterial's degradation mechanism and rate (in vitro and in vivo) and the mechanical properties and biocompatibility in vivo.

Materials and Methods

Synthesis of the Pre-Polymer and Acrylated Pre-Polymer

All chemical were purchased from Sigma-Aldrich (Milwaukee, Wis., USA), unless stated otherwise. Both PGS and PGSA were synthesized substantially as described in, Wang Y, Ameer G A, Sheppard B J, Langer R., Nat. Biotechnol 20(6): pp 602-6 (2002), the entire contents of which are herein incorporated by reference. The PGS pre-polymer was synthesized by polycondensation of equimolar glycerol and sebacic acid (Fluka, Buchs, Switzerland) at 120° C. under argon for 24 h before reducing the pressure from 1 torr to 40 mtorr over 5 h. The polycondensation was continued for another 24 h, yielding a viscous pre-polymer. For the PGSA synthesis, the PGS pre-polymer was used without further purification. PGSA was synthesized with a low number of acrylate groups (PGSA-LA) and a high number of acrylate groups (PGSA-HA) on the backbone substantially as described in Example 1. For this purpose, 20 g of the PGS pre-polymer (with 78 mmol hydroxyl groups), 200 mL anhydrous dichloromethane and 4(dimethylamino)pyridine (DMAP) (20 mg, 1.8(10$^{-4}$) mol) were charged into a reaction flask. The reaction flask was cooled to 0° C. wider a positive pressure of nitrogen. For the PGSA-LA, acryloyl chloride (37 mmol) was slowly added parallel to an equimolar amount of triethylamine. For the PGSA-HA acryloyl chloride (48 mmol) was slowly added parallel to an equimolar amount of triethylamine. The reaction was allowed to reach room temperature and was stirred for an additional 24 h. The resulting mixture was dissolved in ethyl acetate, filtered and dried at 45° C. and 5 Pa.

Photocured PGSA-LA and PGSA-HA sheets were formed by mixing PGSA with 0.1% (wt/wt) photoinitiator (2,2-dimethoxy-2-phenyl-acetophenone) and the polymerization reaction initiated by ultraviolet light, at a power density of about 4 mW/cm², from a ultraviolet lamp (model 100AP, Blak-Ray), between two glass slides with a 1.6 mm spacer, for 10 minutes. PGSA-LA mixed with 0.1% photo initiator (wt/wt) and 5% (wt/wt) PEG-diacrylate (Mw=700 Da) was photocured as described for PGSA-LA/HA. 1.6 mm PGS pre-polymer sheets were thermally cured at 140° C. and 40 mtorr for 16 h. The polymer sheets were washed in 100% ethanol for 24 h. to remove any unreacted macromers or photo initiator and dried in the oven at 60° C. for 24 h. 48 h prior to in vivo implantation, the polymer sheets were UV radiated in a laminar flow hood for 40 min. to sterilize the sheets, and then washed in 100, 70, 50, 30% (ethanol/sterile phosphate buffer saline (PBS)) for 10 min. and placed in sterile PBS.

Characterization of the Pre-Polymer and Acrylated Pre-Polymer

Characterization of the pre-polymers and polymers was conducted substantially as described in Example 1.

Implantation

Young adult female Lewis rats (Charles River Laboratories, Wilmington, Mass.) weighing 200-250 g were housed in groups of 2 and had access to water and food ad libitum. Animals were cared for according to the approved protocols of the Committee on Animal Care of the Massachusetts Institute of Technology in conformity with the NIH guidelines for the care and use of laboratory animals (NIH publication #85-23, revised 1985). The animals were anaesthetized using continuous 2% isoflurane/$O_2$ inhalation. Two rats per group per time point received implants. This was done by two small midline incisions on the dorsum of the rat and the implants were introduced in lateral subcutaneous pockets created by blunt dissection. The skin was closed using staples or a single 2-0 Ethilon suture. The cranial implants were used for histology and were resected en bloc with surrounding tissue. The caudal implants were harvested for the assessment of degradation and mechanical testing. Each side of the rat carried PGS, PGSA-LA, PGSA-HA or PGSA-PEG implants. Every 7 days the animals were briefly anaesthetized and shaved for inspection and palpation of the implants to assess any wound healing problems and gross implant dimensions.

In Vitro and In Vivo Degradation

To assess degradation via hydrolysis and enzymes in vitro, cylindrical slabs of dried PGS, PGSA-LA, PGSA-HA and PGSA-PEG (diameter 10×1.6 mm) (n=3) were weighed ($W_0$) and immersed in 5 mL of PBS, pH 7.4 and in 2 ml PBS with 40 units (94.7 mg) of cholesterol-esterase at 37° C. For the degradation in PBS, time points were taken at 0 and 10 weeks and for the enzymatic degradation at (4.5, 9, 14, 24 and 48 h.). All samples were washed with deionized water and surface water was removed with tissue paper. Samples were then dried at 90° C. for 3 days and weighed (Wt) again. The mass loss $[((Wt-W_0)/W_0)\times100]$ was calculated. For the in vivo degradation study, cylindrical slabs of dried photocured PGS, PGSA-LA, PGSA-HA and PGSA-PEG (diameter 10×1.6 mm) (n=4) were implanted. To accesses in viva degradation PGS, PGSA-LA, PGSA-HA and PGSA-PEG implants were isolated from the surrounding tissue and collected in PBS. After surgical removal, the explants were weighed (Wt) and sized (St) between two microscope cover slides. Compression tests were performed on the explants (wet) with a 50N load at a compression rate of 5 mm/min using an Instron 5542, substantially according to ASTM standard D575-91. Samples were compressed 40%, compression modulus was calculated from the initial slope (0-10%) of the stress-strain curve. The explants were then weighed (Ww), dried at 90° C. for 3 days and weighed (Wt) again. The water content $[((Ww-Wt)/Wt)\times100]$, mass loss $[((Wt-W_0)/W_0)\times100]$ and size over time $[((St-S_0)/S_0)\times100]$ were calculated, where $S_0$ represents the size of the implant prior to implantation.

All the explants were cut in half by a razorblade. One half of each of the explants were prepared for scanning electron microscope (SEM), sputter-coated with platinum/palladium (about 250 Angstrom layer), mounted on aluminum stubs with carbon tape and examined on a JEOL JSM-5910. The other half was used to accesses the sol content of the material. For this purpose, the dry explants were weighed (Wd), placed in 100% ethanol for 3 days on a orbital shaker, dried at 90° C. for 3 days and weighed (Ws) again to determine the sol content of the explants by $[((Wd-Ws)/Ws)\times100]$.

In Vivo Biocompatibility

Specimens for histology were fixed using a 10% formaldehyde solution and prepared for immunohistochemical staining analysis. The sections were stained using heamatoxylin and eosin (H&E). The H&E stained sections were analyzed by a medical doctor experienced in pathology who was blinded as to the polymer content of the implants. The H&E stains were used to analyze for the presence of fibroblasts in the capsule surrounding the material, macrophages in contact with the material, and for the presence of multinucleated giant cells, ingrowth of cells into the material and phagocytosis of the material.

Statistical Analysis

Statistical analysis was performed using a homoscedastic two-tailed Student's t-test with a minimum confidence level of 0.05 for statistical significance. All values are reported as the mean and standard deviation.

Results

In the following discussion of the results of Example 2, the abbreviation PGSA will refer to photocured poly(glycerol sebacate)-acrylate elastomers and the consecutive abbreviation LA or HA will refer to degree of acrylation (low or high) on the backbone of the PGS pre-polymer. PGSA-PEG will refer to the photocrosslinked copolymer from PGSA-LA (low degree of acrylation) and 5% (wt/wt) poly(ethelyne glycol) PEG diacrylate. PGS will refer to the thermally cured elastomer.

Polymer Characterization

The PGS pre-polymer had a molar composition of approximately 1:1 glycerol:sebacic acid as evidenced by $^1$H-NMR analyses. The incorporation of acrylate groups was confirmed by $^1$H-NMR by the appearance of the peaks at d 5.9, 6.1 and 6.4 ppm. The degree of acrylation (i.e. ratio of acrylate groups to glycerol moieties) on the backbone of the pre-polymer was calculated from the proportion of signal intensities on $^1$H-NMR, and was 0.31±0.02 for PGSA-LA and 0.41±0.03 for PGSA-HA.

The UV polymerization of PGSA in the presence of the photoinitiator 2-dimethoxy-2-phenyl-acetophenone yielded elastomeric networks, as did thermally cured PGS. The viscous PGSA pre-polymers formed a clear elastomeric slab within 10 minutes, whereas PGS required 16 h of curing. Increasing the density of the acrylate groups in the pre polymer increases, it is believed without being held to theory, the length and density of the methylene chains in the network that is formed, which it is believed, without being held to theory, could slow the degradation of the biomaterial. The mechanical and thermal properties of the elastomers are summarized in Table 2.

TABLE 2

| | Degree of acrylation | Tg (° C.) | Young's modulus (Mpa) | Elongation (%) | Crosslinking density (mol/m3) |
|---|---|---|---|---|---|
| PGS | — | −28 | 0.76 | 80 | 102 |
| PGSA-LA | 0.31 | −32 | 0.38 | 55 | 51.5 |
| PGSA-HA | 0.41 | −31 | 0.89 | 51 | 120 |
| PGSA-PEG | 0.31 | −32 | 0.8 | 45 | 108 |

In Vitro Degradation Results

Figure 15:
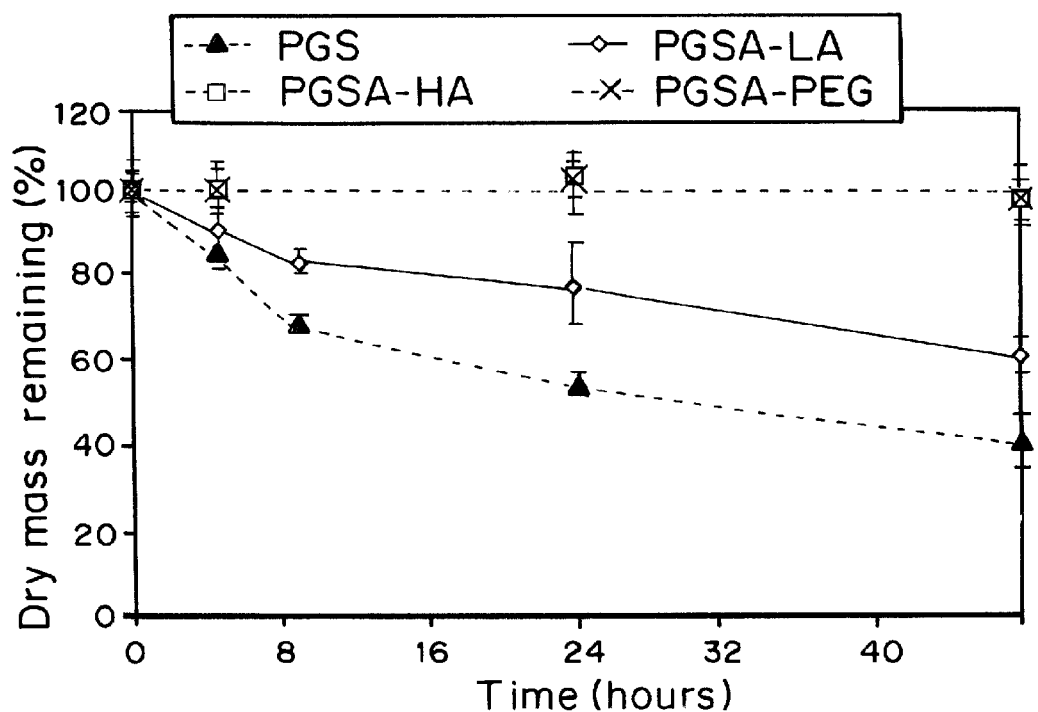
FIG. 15 presents data on the enzymatic degradation by cholesterol esterase (pH 7.2, 37° C.)(n=3) as further described in Example 2.

Photocured PGSA and PGSA-PEG samples showed a 5-10% mass loss in PBS over a period of ten weeks. The hydrolytic degradation of PGSA was observed to decrease when the degree of acrylation was increased or when PEG was incorporated. The potential contribution of enzymatic activity to the degradation of these elastomers was assessed by incubation in 40 units of pancreatic cholesterol esterase in 2 ml PBS. Pancreatic cholesterol esterase has been reported to be substantially identical to the esterases associated with macrophages (inflammatory cells) known to degrade polyesters. PGS and PGSA-LA showed a mass loss over time, while PGSA-HA and PGSA-PEG did not. PGS degraded by 60% over 48 h, while PGSA-LA, which has a lower crosslinking density, only degraded by 40% (data is presented in FIG. 15). The results suggest that the long methylene cross-links formed from acrylate groups are less susceptible to cholesterol esterase than the cross-links formed in PGS.

In Vivo Degradation Results

To assess the degradation characteristics of PGS, PGSA and PGSA-PEG copolymer in vivo, discs of cross-linked material were implanted subcutaneously in rats, and harvested at predetermined intervals. On dissection, the caudal implants were easily separated from surrounding tissue. The geometry and surface properties of the explants were examined and changes in mass, water content, sol content and mechanical strength over time were observed (data is presented in FIGS. 16A-D and 17).

Incorporation of acrylate groups or PEG into the backbone was observed to decrease the degradation of the material (see FIG. 16A): 80% of PGS mass degraded within 5 weeks, while the same mass loss occurred for PGSA-LA over 9 weeks. PGSA-HA degraded even slower with an initial 5% mass loss in the first 5 weeks, followed by an accelerated mass loss to 60% at 11 weeks. Degradation was further delayed with the incorporation of PEG in the polymer chain, with a mass loss of approximately 20% after 12 weeks in viva. After 3 weeks in vivo: PGSA-PEG and PGSA-HA mass loss was not significantly different and significantly lower than PGS and PGSA-LA, while PGS mass loss was significantly higher than that of PGSA-LA (p=0.034). After 11 weeks in vivo PGSA-HA mass loss was significantly higher than PGSA-PEG at 12 weeks in vivo (p<0.001).

Figure 16A:
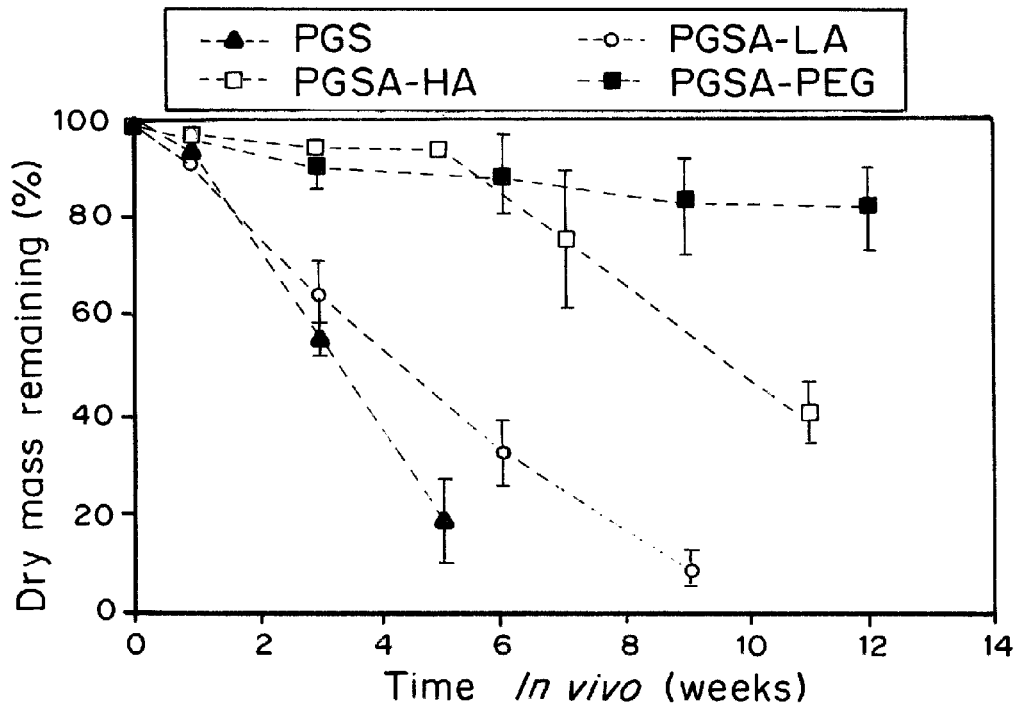
FIGS. 16A-D present data, as further described in Example 2, comparing.
Figure 16B:
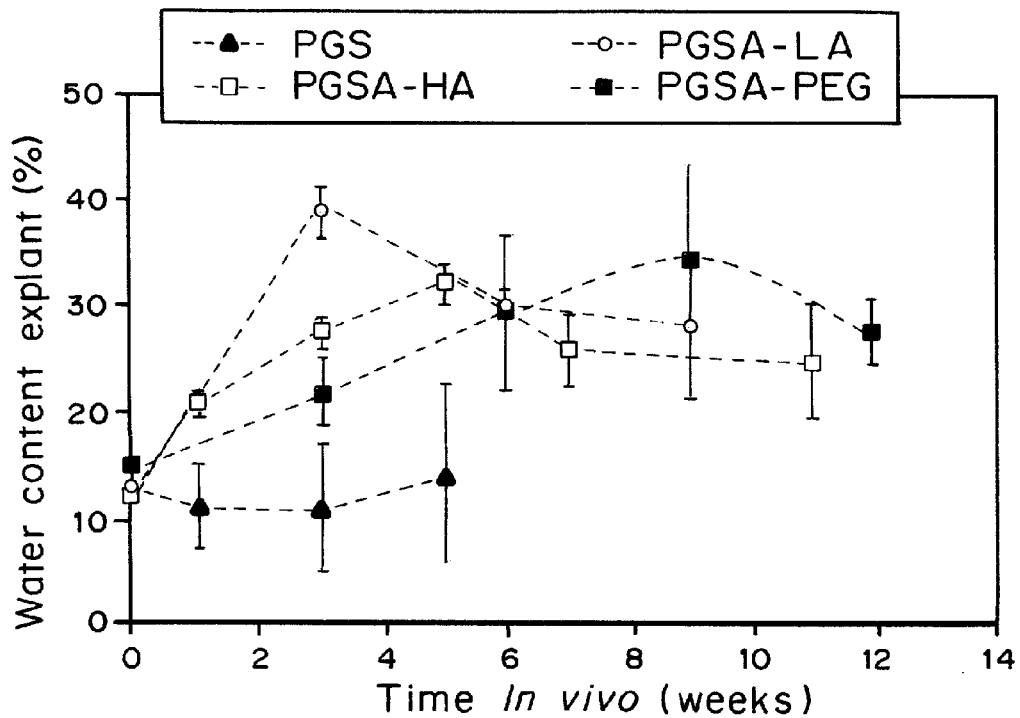

PGS showed constant water content over time, whereas the water content of all photocured elastomers rose initially and then declined (see FIG. 16B). The time to peak water content was observed to follow the order PGSA-LA<PGSA-HA<PGSA-PEG.

Figure 16C:
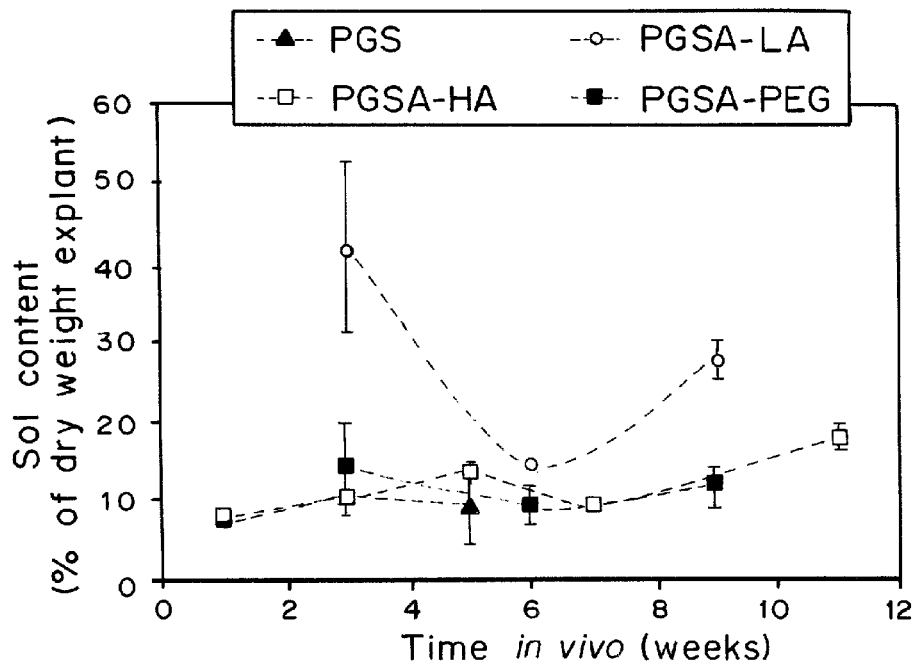
Figure 16D:
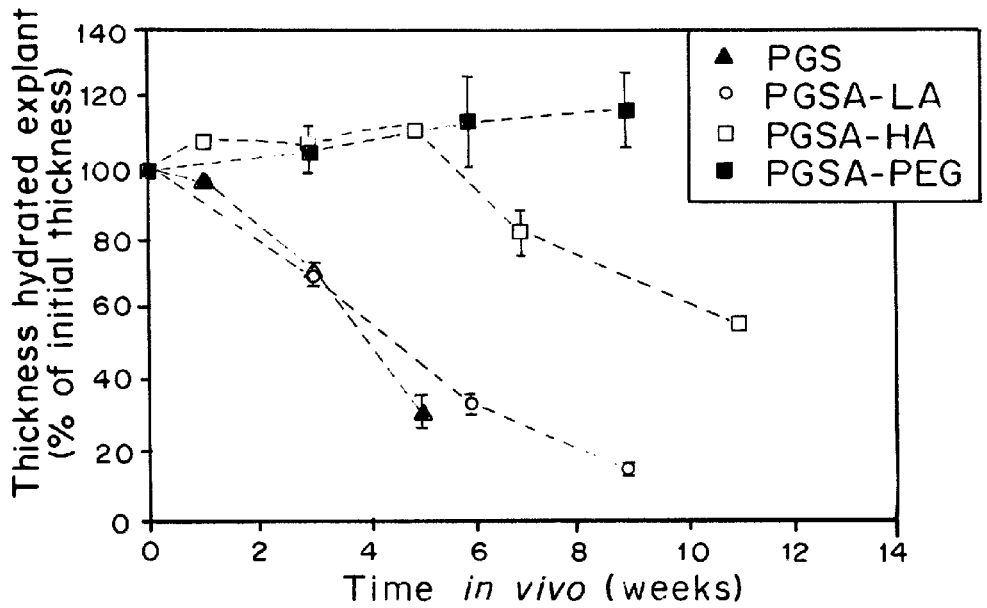

The sol content (macromers not connected to the backbone of the material) of PGSA-HA and PGSA-PEG, were comparable to the sot content of PGS (p>0.05) (see FIG. 16C). The average sol content of PGSA-LA over time was significantly higher than that of the other elastomers (p<0.001).

The thickness of the implanted discs of PGS and PGSA-LA (see FIG. 16D) decreased rapidly. At week 7, the thickness of PGSA-HA discs was significantly lower than the initial thickness of the implants (p<0.01). The thickness of PGSA-PEG discs was essentially unchanged over time (p>0.05). These findings correlate with the patterns of dry mass remaining (see FIG. 16A).

The mechanical strength of PGSA-LA and PGS decrease (data is presented in FIG. 17): at 3 weeks in vivo PGS and PGSA has lost 40%, while both PGSA-HA and PGSA-PEG lost only 13% of its original strength (p<0.004). PGSA-HA at 11 weeks in vivo lost >90% of its original strength while PGSA-PEG only lost 40% of its original strength at 12 weeks in vivo (p<0.001). Similar to the thickness of the polymeric discs, the mechanical strength over time in vivo (see FIG. 17) approximately follows the same patterns as the mass remaining (see FIG. 16A).

SEM analysis of the cross-section (data is presented in FIGS. 18A-H) of PGS, PGSA-LA and PGSA-HA indicates that the structural integrity is maintained, while up to 80% of the material is degraded. In contrast, PGSA-PEG shows formation of pores within the bulk of the material after 9 weeks in vivo. SEM analysis of the surface of PGS, PGSA-LA, PGSA-HA and PGS-PEG shows a comparable surface topography (data is presented in FIGS. 19A-D).

Figure 17:
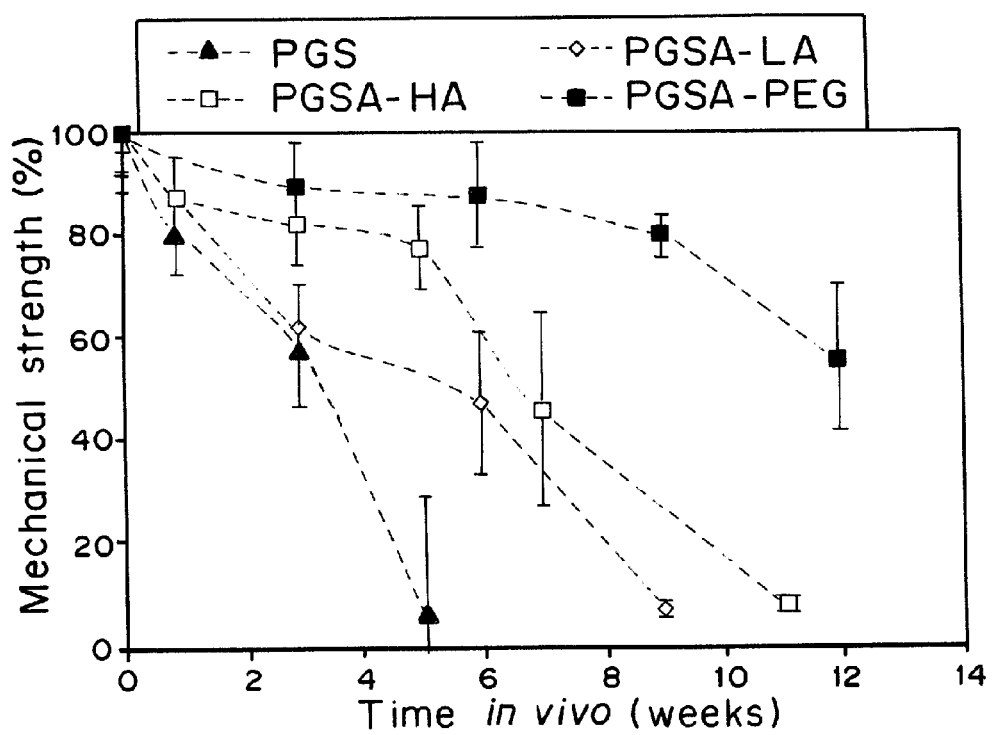
FIG. 17 presents data, as further described in Example 2, on the changes in mechanical strength of PGS, PGSA-LA, PGSA-HA and PGSA-PEG during in vivo degradation (n=4).

Degradation of PGS (the positive control for a surface eroding polymer) showed a linear decrease in mass remaining (see FIG. 16A), a constant and low water content of the explants over time (see FIG. 16B), a linear decrease of the discs thickness (see FIG. 16D) and a linear mechanical strength loss over time (see FIG. 17). Due to the relatively fast degradation at the surface the mass loss is linear and the sol content and water content remains low and constant. The decrease in mechanical strength (see FIG. 17) is believed to be due to hydrolysis where bonds are cleaved within the bulk. These results, together with the slow in vitro degradation in PBS suggest that the degradation mechanism of PGS in vivo is predominantly enzymatic surface degradation. However, during enzymatic surface degradation, it is believed bonds are being cleaved due to hydrolysis in the bulk of the material.

For the photocured elastomers, incorporation of acrylate groups in the PGS pre-polymer and subsequent photocuring decreased the degradation rate in vivo (see FIG. 16A). Although, the crosslinking density of PGSA-LA is lower than PGS (see Table 1), the degradation of PGSA-LA is slower. It is believed, without being held to theory, that this is due at least in part to the methylene cross-links in PGSA degrading slower than the original PGS cross-links. The methylene cross-links was observed to affect the degradation profile; PGSA-LA shows a linear mass loss over time, while PGSA-HA shows an initial 5% mass loss in the first 5 weeks, followed by an accelerated linear mass loss (see FIGS. 16A-D).

The degradation mechanism of these photocured polymers is not obvious. PGSA-LA shows a typical degradation profile for surface degradation: structural integrity during degradation (see FIGS. 18B and 18F), linear mass loss and linear size loss over time (see FIGS. 16A and 16D). However, the water content and sol content changes drastically over, time (see FIGS. 16B and 16C). Therefore, it is believed, without being held to theory, that the degradation of PGSA-LA is due to both surface and bulk degradation.

PGSA-HA showed a bulk degradation profile with at first an increasing water content followed by an accelerated mass loss in time. The mechanical properties of the PGSA-HA samples were 77% of their original strength at 5 weeks, while the mass loss was only 5%. However, the structural integrity of the PGSA-HA discs and the sol content over time does not point towards bulk degradation (see FIGS. 16C, 18C and 18H). It is believed, without being held to theory, that the initial 5% mass loss of PGSA-HA (first 5 weeks) is due largely to hydrolysis in the bulk, decreasing its crosslink density (and mechanical strength) and increasing the water content of the PGSA-HA explants. The change in water content and possibly the exposure of the methylene cross-links, after 5 weeks, accelerates the degradation of the photocured cross-links on the surface.

The different profile observed for PGSA-LA and PGSA-HA in the first 5 weeks is comparable to what was observed in vitro. Initially PGSA-LA is degraded by cholesterol esterase, while PGSA-HA is not. This suggests that the degradation of the methylene cross-links on the surface (PGSA-LA and PGSA-HA after 5 weeks) is likely due to enzymes, while the degradation in the bulk of the material for PGSA-LA and PGSA-HA is due to hydrolysis. Which is supported by both the in vitro and in vivo enzymatic degradation of polyesters from the surface. In addition, in vitro and in vivo hydrolytic degradation is observed in the bulk and at the surface.

The copolymerization of PEG-diacrylate with PGSA-LA results in long methylene cross-links (due to acrylate groups) and low molecular PEG chains in the biomaterial's network. The incorporation of the PEG chains in the biomaterial's network decreases the degradation rate substantially (see FIG. 16A). Similar to PGSA-HA, PGSA-PEG shows an initial slow mass loss and an increase in water content over time. Although, the water content of PGSA-PEG has reached its maximum after 9 weeks (see FIG. 16B) an accelerated mass loss has not yet been observed after 12 weeks in vivo (see FIG. 16A). The degradation observed for PGSA-PEG in vivo up to 12 weeks is believed to be largely due to hydrolytic bulk degradation. Degradation of PGSA-PEG was 20% after 12 weeks in vivo while for PGSA-HA, with the same cross-linking density, the degradation was more than 50%. As can be seen, these embodiments provided a decrease in the degradation rate of PGSA independent of the cross-linking density. SEM images of the cross-section of PGSA-PEG explants show pore formation in the explants after 9 weeks in viva (see FIGS. 18D and 18H), which supports the bulk degradation mechanism. The sot content of PGSA-PEG was observed to be not as high as the bulk eroding PGSA-LA. However, this could be due to the greater solubility of macromers which include a short PEG chain, making it difficult to compare the sol content of PGSA-PEG and PGSA.

The degradation rate of the implanted slabs was observed to be dependent on the types of cross-links in the material. An increase in the photo-induced methylene cross-links was observed to result in a decrease in degradation rate. Compared to PGS, the degradation rate of PGSA is slower. Incorporation of PEG has a greater effect; and facilitates decreasing the degradation rate of PGSA substantially independently of the crosslinking density.

The degradation mechanism of the implanted PGSA slabs was also affected. PGS was observe to be degraded by surface degradation. Incorporation of acrylate groups into the PGS backbone was observed to result in a change in the degradation mechanism. Both PGSA-LA and PGSA-HA showed bulk degradation possibly by hydrolysis and a relatively fast surface degradation believed to be due to enzymes. However for PGSA-HA, surface degradation was observed after 5 weeks, whereas PGSA-LA showed both bulk and surface degradation substantially continuously: Incorporation of PEG chains in the biomaterial resulted in predominantly bulk degradation by hydrolysis up to 12 weeks in vivo.

In Vivo Biocompatibility

On dissection, discs of the materials were encased in a translucent tissue capsule, with some vascularity. The surrounding tissues were otherwise normal in appearance, allowing for changes attributable to the implantation process at the earliest time points. The polymeric disks were easily separated from the capsule at all time points. To visual inspection, they were smooth-surfaced initially, then became progressively rougher over time (see FIGS. 18A-H), with a time course that paralleled the mass loss over time (see FIG. 16A). Histological assessment of the cross-linked materials and surrounding tissues showed comparable levels of mild inflammation surrounding all discs that eventually transitioned into a fibrous capsule over time. Fibroblasts were mostly present in fibrous capsule, and no cell in growth in the polymeric discs was observed. The tissues surrounding all the polymeric discs showed no observable injury. Inflammatory cells were commonly found at the interface between the tissues and the degrading polymer. More specifically, when comparing PGS with PGSA-HA (see FIGS. 20A-F), PGS showed a higher inflammatory activity at week 1 and week 3 than PGSA-HA, corresponding to the high mass loss of PGS and the initial low mass loss of PGSA-HA. However, after 5 weeks, PGSA-HA showed a similar inflammatory response compared to PGS at week 1 and 3. PGSA-LA showed a greater inflammatory activity from week 1, compared to PGSA-PEG (see FIGS. 21A-F) inflammatory cells were predominantly located between the fibrous capsule and tissue polymer interface for PGS, PGSA-LA and PGSA-HA (after week 5). While for PGSA-HA (before week 7) and PGSA-PEG the fibrous capsule was directly on the tissue polymer interface (see FIGS. 20A-F, 21A-F). This indicates that the presence of inflammatory cells was associated with the degradation of PGS, PGSA-LA and PGSA-HA (after 5 weeks). As it is believed that inflammatory cells are associated with a high activity of cholesterol esterase, these results support the belief that the high mass loss over time in vivo is due to enzymatic degradation.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present inventions be limited to such embodiments or examples. On the contrary, the present inventions encompass various alternatives, modifications, and equivalents, as will be appreciated by those of skill in the art.

While the present inventions have been particularly shown and described with reference to specific illustrative embodiments, it should be understood that various changes in form and detail may be made without departing from the spirit and scope of the present inventions. Therefore, all embodiments that come within the scope and spirit of the present inventions, and equivalents thereto, are claimed. The claims, descriptions and diagrams of the methods, systems, and assays of the present inventions should not be read as limited to the described order of elements unless stated to that effect.

What is claimed is:

1. A method comprising contacting tissue with a cross-linkable polyester prepolymer,
wherein the cross-linkable polyester prepolymer comprises a polymeric unit of the general formula $$(\text{-A-B-})_n,$$

wherein A represents a substituted or unsubstituted ester, wherein A comprises a free hydroxyl group prior to cross-linking, B represents a substituted or unsubstituted ester comprising at least two acid ester functionalities, n represents an integer greater than 1, and cross-linking the cross-linkable polyester pre-polymer between a plurality of the A components of the polyester to form an adhesive, wherein the cross-links contain a single dioic acid ester functionality.

2. The method of claim 1, wherein the cross-linked polyester has the general formula (I)

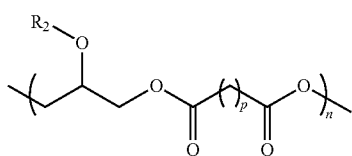

(I)

wherein p and n each individually represent an integer greater than 1,

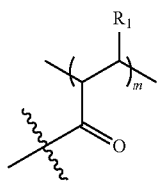

wherein $R_2$ in each individual unit is hydrogen or wherein m represent an integer greater than 1, and $R_1$ is hydrogen or methyl.

3. The method of claim 2, wherein p=8.

4. The method of claim 1, wherein the average ratio of the number of cross-links to the number of $(-A-B-)_n$ polymeric units is less than about 0.4.

5. The method of claim 1, wherein the average ratio of the number of cross-links to the number of $(-A-B-)_n$ polymeric units is greater than about 0.5.

6. The method of claim 1, wherein the cross-linked polyester is cross-linked to a substituted or unsubstituted alkane through at least a portion of the A components of the polyester.

7. The method of claim 1, wherein a plurality of unit A of the cross-linkable polyester pre-polymer comprise an acrylate group and the acrylate groups are cross-linked to form the adhesive.

8. The method of claim 7, wherein the cross-linked polyester has the general formula (II)

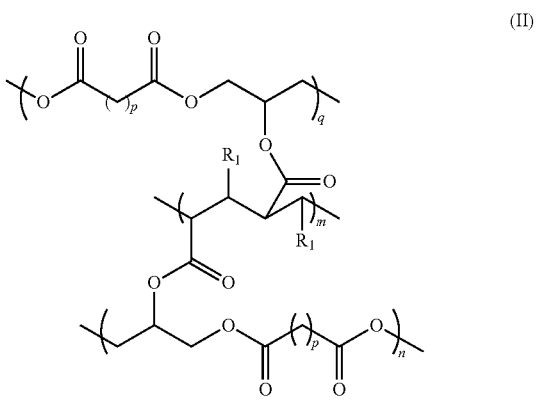

(II)

wherein m, n, p, and q each independently represent an integer greater than 1, and $R_1$ is hydrogen or methyl.

9. The method of claim 8, wherein p=8.

10. The method of claim 1, wherein the cross-link density is less than 1%.

11. The method of claim 10, wherein the cross-link density is less than 0.5%.

12. The method of claim 11, wherein the cross-link density is less than 0.05%.

13. The method of claim 1, wherein the adhesive is one or more of non-toxic to humans, biocompatible, and bioabsorbable.

14. The method of claim 1, wherein the adhesive promotes hemostasis.

15. The method of claim 1, wherein the adhesive promotes wound closure.

16. The method of claim 1, wherein the adhesive adheres a medical device to tissue.

17. The method of claim 1, wherein the cross-linkable polyester pre-polymer is at least partially cross-linked in vivo.

* * * * *

UNITED STATES PATENT AND TRADEMARK OFFICE
CERTIFICATE OF CORRECTION

PATENT NO. : 8,691,203 B2
APPLICATION NO. : 13/428869
DATED : April 8, 2014
INVENTOR(S) : Bettinger Page 1 of 1

It is certified that error appears in the above-identified patent and that said Letters Patent is hereby corrected as shown below:

In the specification

Column 1, lines 18-25, delete the paragraph titled "GOVERNMENT SUPPORT":

"The United States Government has provided grant support utilized in the development of one or more of the present inventions. In particular, National Institute of Health (NIH) contract number DE 013023 and National Science Foundation (NSF) contract number NIRT 0609182 have supported development of one or more of the inventions of the present application. The United States Government may have certain rights in these inventions."

and replace with:

--This invention was made with Government support under Grant No. R01 DE013023 awarded by the National Institutes of Health and under Grant No. BES0609182 awarded by the National Science Foundation. The Government has certain rights in the invention.--.

Signed and Sealed this
Twenty-second Day of March, 2016

Michelle K. Lee
*Director of the United States Patent and Trademark Office*